(12) United States Patent
Zhang et al.

(10) Patent No.: US 11,807,615 B2
(45) Date of Patent: Nov. 7, 2023

(54) COMPOUND, ORGANIC ELECTROLUMINESCENT DEVICE, AND DISPLAY DEVICE

(71) Applicants: Wuhan Tianma Micro-Electronics Co., Ltd., Wuhan (CN); Wuhan Tianma Microelectronics Co., Ltd. Shanghai Branch, Shanghai (CN)

(72) Inventors: Lei Zhang, Shanghai (CN); Wei Gao, Shanghai (CN); Jinghua Niu, Shanghai (CN); Wenpeng Dai, Shanghai (CN); Wenjing Xiao, Shanghai (CN); Yan Lu, Shanghai (CN); Hongyan Zhu, Shanghai (CN)

(73) Assignees: WUHAN TIANMA MICRO-ELECTRONICS CO., LTD., Wuhan (CN); WUHAN TIANMA MICROELECTRONICS CO., LTD. SHANGHAI BRANCH, Shanghai (CN)

( * ) Notice: Subject to any disclaimer, the term of this patent is extended or adjusted under 35 U.S.C. 154(b) by 462 days.

(21) Appl. No.: 16/730,171

(22) Filed: Dec. 30, 2019

(65) Prior Publication Data
US 2021/0122723 A1     Apr. 29, 2021

(30) Foreign Application Priority Data
Oct. 28, 2019   (CN) ......................... 201911030389.3

(51) Int. Cl.
*C07D 307/91* (2006.01)
*C07D 333/76* (2006.01)
(Continued)

(52) U.S. Cl.
CPC ......... *C07D 307/91* (2013.01); *C07D 333/76* (2013.01); *C07D 407/12* (2013.01);
(Continued)

(58) Field of Classification Search
CPC .. C07D 307/77; C07D 307/91; C07D 333/50; C07D 333/76; C07D 405/04;
(Continued)

(56) References Cited

U.S. PATENT DOCUMENTS

| | | | |
|---|---|---|---|
| 8,431,250 B2 * | 4/2013 | Mizuki | H01L 51/006 |
| | | | 313/506 |
| 2007/0278938 A1 * | 12/2007 | Yabunouchi | H05B 33/14 |
| | | | 313/504 |

(Continued)

FOREIGN PATENT DOCUMENTS

| | | | |
|---|---|---|---|
| CN | 107652224 A | | 2/2018 |
| KR | 20100123172 A | * | 11/2010 |

(Continued)

OTHER PUBLICATIONS

Machine translation of WO 2019/083167 A1 (publication date May 2019). (Year: 2019).*

(Continued)

*Primary Examiner* — Dawn L Garrett
(74) *Attorney, Agent, or Firm* — Anova Law Group, PLLC

(57) ABSTRACT

The present disclosure provides a compound having a formula (I):

formula (I)

(Continued)

wherein $C_y$ represents substituted or unsubstituted C5-C40 aryl; X represents oxygen atom or sulfur atom; $L_1$ is selected from substituted or unsubstituted C5-C40 aryl, or substituted or unsubstituted C3-C40 heteroaryl; A includes a structure represented by formula (II):

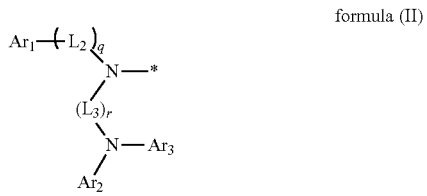

formula (II)

wherein each of $L_2$ and $L_3$ is independently selected from substituted or unsubstituted C5-C40 aryl, or substituted or unsubstituted C3-C40 heteroaryl; each of $Ar_1$, $Ar_2$, and $Ar_3$ is independently selected from substituted or unsubstituted C5-C40 aryl, substituted or unsubstituted C3-C40 heteroaryl, or substituted or unsubstituted arylamine containing one or two nitrogen atoms; each of m, q, and r is independently selected from 0 or 1; and * indicates a connection position.

14 Claims, 1 Drawing Sheet

(51) Int. Cl.
| | |
|---|---|
| *C07D 407/12* | (2006.01) |
| *C07D 409/14* | (2006.01) |
| *H10K 50/11* | (2023.01) |
| *H10K 50/15* | (2023.01) |
| *H10K 85/60* | (2023.01) |
| *H10K 50/16* | (2023.01) |

(52) U.S. Cl.
CPC ........... *C07D 409/14* (2013.01); *H10K 50/11* (2023.02); *H10K 50/156* (2023.02); *H10K 85/633* (2023.02); *H10K 85/636* (2023.02); *H10K 85/654* (2023.02); *H10K 85/6574* (2023.02); *H10K 85/6576* (2023.02); *H10K 50/15* (2023.02); *H10K 50/16* (2023.02)

(58) Field of Classification Search
CPC .. C07D 407/12; C07D 409/12; C07D 409/14; H01L 51/006; H01L 51/0061; H01L 51/0067; H01L 51/0073; H01L 51/0074; H01L 51/5012; H01L 51/5056; H01L 51/5064; H01L 51/5072; H10K 50/11; H10K 50/156; H10K 85/633; H10K 85/636; H10K 85/654; H10K 85/6574; H10K 85/6576; H10K 50/15; H10K 50/16
See application file for complete search history.

(56) References Cited

U.S. PATENT DOCUMENTS

| | | | | |
|---|---|---|---|---|
| 2018/0072695 | A1* | 3/2018 | Byun | C07D 409/14 |
| 2020/0106021 | A1* | 4/2020 | Kim | H01L 51/0073 |
| 2020/0365815 | A1* | 11/2020 | Oh | H01L 51/0005 |

FOREIGN PATENT DOCUMENTS

| | | | | |
|---|---|---|---|---|
| KR | 20160059609 A | * | 5/2016 | |
| WO | WO-2018016786 A1 | * | 1/2018 | ........... C07C 211/54 |
| WO | WO-2019083167 A1 | * | 5/2019 | ............. C09K 11/06 |

OTHER PUBLICATIONS

Machine translation for KR 20160059609 A (publication date: May 2016). (Year: 2016).*
Machine translation for KR 20100123172 A (publication date: Nov. 2010). (Year: 2010).*

* cited by examiner

COMPOUND, ORGANIC ELECTROLUMINESCENT DEVICE, AND DISPLAY DEVICE

CROSS-REFERENCES TO RELATED APPLICATION

This application claims the priority of Chinese Patent Application No. 201911030389.3, filed on Oct. 28, 2019, the content of which is incorporated by reference in its entirety.

TECHNICAL FIELD

The present disclosure generally relates to the field of organic electroluminescence and, more particularly, to a compound, an organic electroluminescent device, and a display device including the same.

BACKGROUND

OLED screens in mobile phones and other small and medium sized consumables use a display mode with R, G, and B subpixels. In order to improve production yield, some functional layers are often formed as known layers so that less FMM (i.e., fine metal mask) are used. A hole transport layer often uses a known layer. Generally, a known hole transport layer can use commercially available materials.

There are several problems with current hole transport materials, including 1) poor material solubility that leads to poor cleaning effect on vapor deposition masks during mass productions; 2) low mobility rate that leads to excessive overall device voltage; 3) over-fast mobility rate, especially sideway-mobility rate, that leads to crosstalk between adjacent pixels; and 4) low triplet energy level that leads to impossible effective transmission of holes in RGB three colors at the same time, leading to increased number of masks and increased process difficulty.

SUMMARY

One aspect of the present disclosure provides a compound having a formula (I):

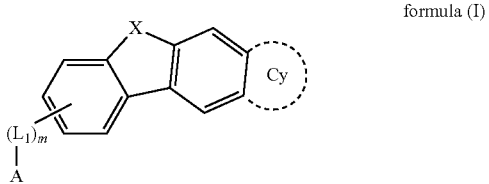

formula (I)

wherein $C_y$ represents substituted or unsubstituted C5-C40 aryl; X represents oxygen atom or sulfur atom; $L_1$ is selected from substituted or unsubstituted C5-C40 aryl, or substituted or unsubstituted C3-C40 heteroaryl; A includes a structure represented by formula (II):

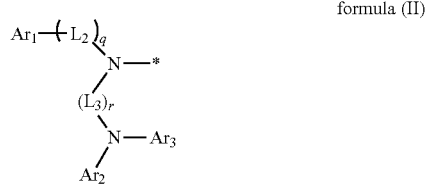

formula (II)

wherein each of $L_2$ and $L_3$ is independently selected from substituted or unsubstituted C5-C40 aryl, or substituted or unsubstituted C3-C40 heteroaryl; each of $Ar_1$, $Ar_2$, and $Ar_3$ is independently selected from substituted or unsubstituted C5-C40 aryl, substituted or unsubstituted C3-C40 heteroaryl, or substituted or unsubstituted arylamine containing one or two nitrogen atoms; each of m, q, and r is independently selected from 0 or 1; and * indicates a connection position.

Another aspect of the present disclosure provides an organic electroluminescence device including a first electrode and a second electrode, and an organic functional layer between the first electrode and the second electrode. The organic functional layer includes a hole transport layer, wherein the hole transport layer is made of a material including a compound having the formula (I).

Another aspect of the present disclosure provides a display device including the organic electroluminescent device according to the present disclosure.

Other aspects or embodiments of the present disclosure can be understood by those skilled in the art in light of the description, the claims, and the drawings of the present disclosure.

BRIEF DESCRIPTION OF THE DRAWINGS

The following drawings are merely examples for illustrative purposes according to various disclosed embodiments and are not intended to limit the scope of the present disclosure.

DETAILED DESCRIPTION

Figure 1:
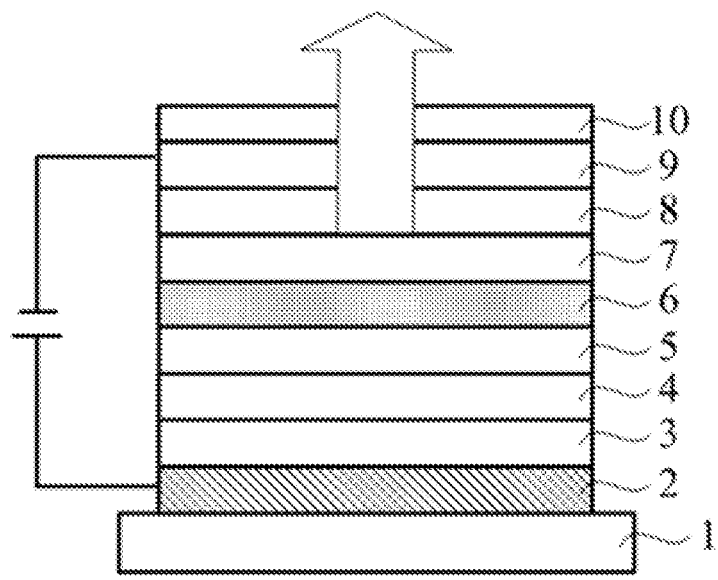
FIG. 1 illustrates an exemplary structure of an organic electroluminescence device consistent with various disclosed embodiments of the present disclosure.

Reference will now be made in detail to exemplary embodiments of the disclosure, which are illustrated in the accompanying drawings. Wherever possible, the same reference numbers will be used throughout the drawings to refer to the same or like parts.

In one embodiment, the present disclosure provides a compound, an organic electroluminescent device including the compound, and a display device having the organic electroluminescent device.

In a specific embodiment, the present disclosure provides a compound having a formula (I),

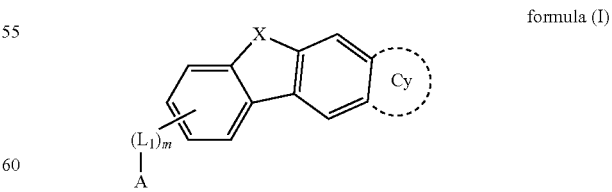

formula (I)

wherein $C_y$ represents substituted or unsubstituted C5-C40 aryl; X represents oxygen atom or sulfur atom; $L_1$ is selected from substituted or unsubstituted C5-C40 aryl, or substituted or unsubstituted C3-C40 heteroaryl; A includes a structure represented by formula (II),

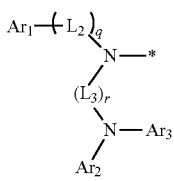

formula (II)

wherein each of $L_2$ and $L_3$ is independently selected from substituted or unsubstituted C5-C40 aryl, substituted or unsubstituted C3-C40 heteroaryl; each of $Ar_1$, $Ar_2$, and $Ar_3$ is independently selected from substituted or unsubstituted C5-C40 aryl, substituted or unsubstituted C3-C40 heteroaryl, or substituted or unsubstituted arylamine containing one or two nitrogen atoms; each of m, q, and r is independently selected from 0 or 1; and * indicates a connection position.

In the present disclosure, the C5-C40 aryl includes monocyclic aromatic hydrocarbon groups and fused ring aromatic hydrocarbon groups, and may be selected from one or more of phenyl, biphenyl, 9,9-fluorenyl, benzene terphenyl, naphthyl, anthracenyl, phenanthryl, 9,10-benzophenanthryl, 1,2-benzophenanthryl, pinenyl, fluorenyl, fluorenyl, and indenyl.

The C3-C40 heteroaryl may be selected from one or more of furyl, thienyl, pyrrolyl, oxazolyl, thiazolyl, pyrazolyl, pyranyl, imidazolyl, pyridyl, pyrazinyl, pyrimidinyl, 1,3,4-oxadiazolyl, 1,2,4-triazolyl, 1,3,5-triazinyl, indolyl, benzimidazolyl, dibenzofuranyl, dibenzothienyl, carbazolyl, quinolyl, quinoxalinyl, o-phenanthroline, phenazinyl, pyridazinyl, or the like.

The term "arylamine containing one nitrogen atom" is used to indicate a following structure:

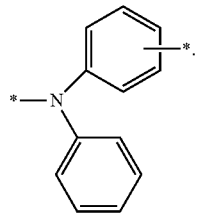

The term "arylamine containing two nitrogen atoms" is used to indicate a following structure:

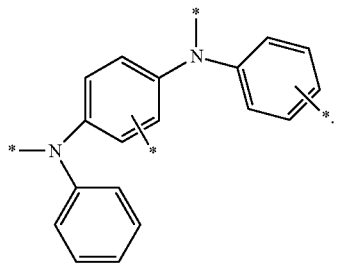

In one embodiment of the present disclosure, "arylamine containing one nitrogen atom or two nitrogen atoms" may be "anilino group containing one nitrogen atom or two nitrogen atoms".

In the present disclosure, unless otherwise specified, substituents in the "substituted . . . " may be one or more of C1-C10 alkyl, C3-C10 cycloalkyl, C2-C10 alkenyl, C1-C6 alkoxy, halogen, cyano, C6-C30 monocyclic aromatic hydrocarbon or fused ring aromatic hydrocarbon group, C3-C30 monocyclic heteroaromatic hydrocarbon or fused ring heteroaromatic hydrocarbon group.

The C1-C10 alkyl includes methyl, ethyl, propyl, isopropyl, butyl, isobutyl, C1-C6 alkyl, C1-C4 alkyl, or the like.

The C3-C10 cycloalkyl includes cyclopropyl, cyclobutyl, cyclopentyl, cyclohexyl, C3-C8 cycloalkyl, C3-C6 cycloalkyl, or the like.

The C2-C10 alkenyl includes vinyl, propenyl, butenyl, C2-C6 alkenyl, C2-C4 alkenyl, or the like.

The C1-C6 alkoxy includes methoxy, ethoxy, propoxy, isopropoxy, butoxy, isobutoxy, C1-C4 alkoxy, or the like.

The halogen includes fluorine, chlorine, bromine, and/or iodine.

In the present disclosure, in the case the connection position is not clearly indicated, or the connection position is indicated by # and *, groups and substituents may be connected to each other at any position, as long as corresponding compounds can be synthesized.

In one embodiment, the substituted or unsubstituted C3-C40 heteroaryl for each of $Ar_1$, $Ar_2$, and $Ar_3$ contains a heteroatom including one or more of P, S, N, O, B, and Si.

In one embodiment, Cy is phenyl.

In one embodiment, m is 0.

In one embodiment, r is 1.

In one embodiment, $Ar_1$ is phenyl.

In one embodiment, each of $Ar_2$ and $Ar_3$ is independently selected from any one of phenyl, biphenyl, dibenzofuranyl, fluorenyl, and pyridyl.

In one embodiment, each of $L_1$, $L_2$, and $L_3$ is independently selected from one or more of the following:

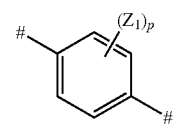

2-1

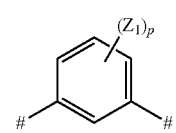

2-2

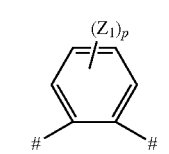

2-3

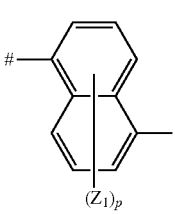

2-4

2-5
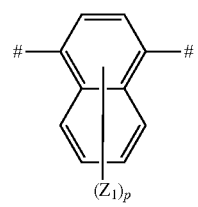
2-6
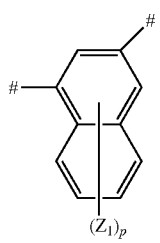
2-7
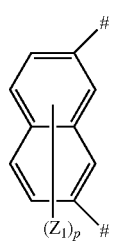
2-8
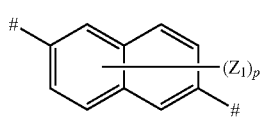
2-9
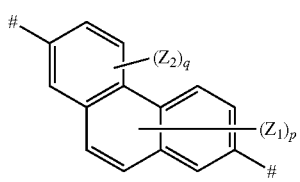
2-10
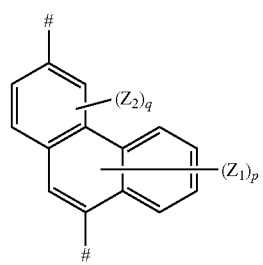
2-11
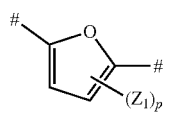
2-12
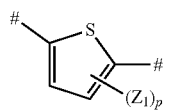
2-13
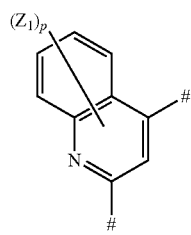
2-14
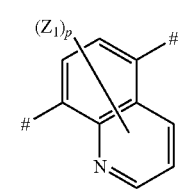
2-15
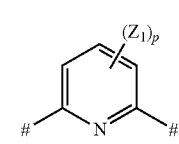
2-16
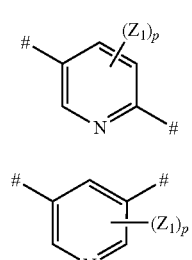
2-17
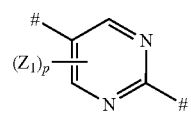
2-18
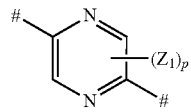
2-19
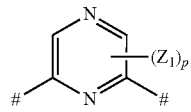
2-20
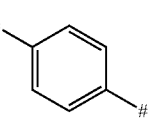
wherein $Z_1$ is selected from substituted or unsubstituted C5-C40 aryl, or substituted or unsubstituted C3-C40 heteroaryl, p is selected from 0, 1 or 2, and # indicates a connection position.
In one embodiment, each of $L_1$, $L_2$, and $L_3$ is independently selected from one or more of the following:
3-1

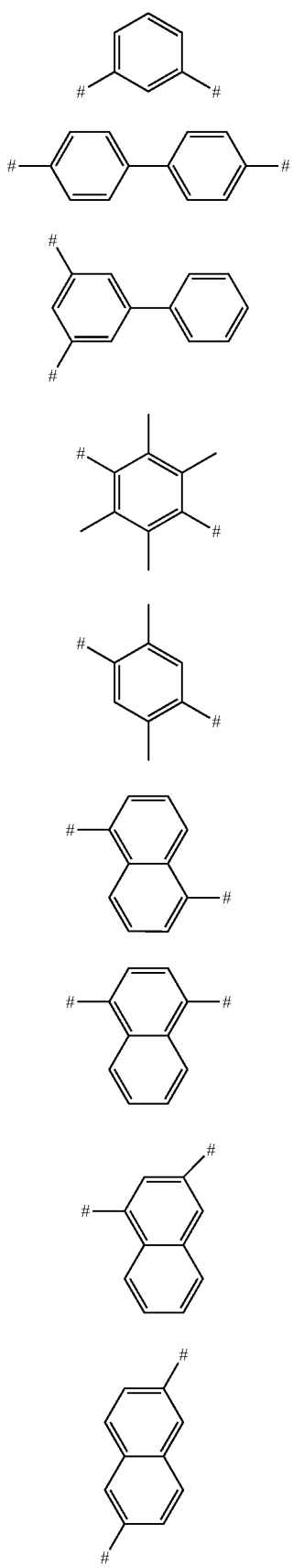
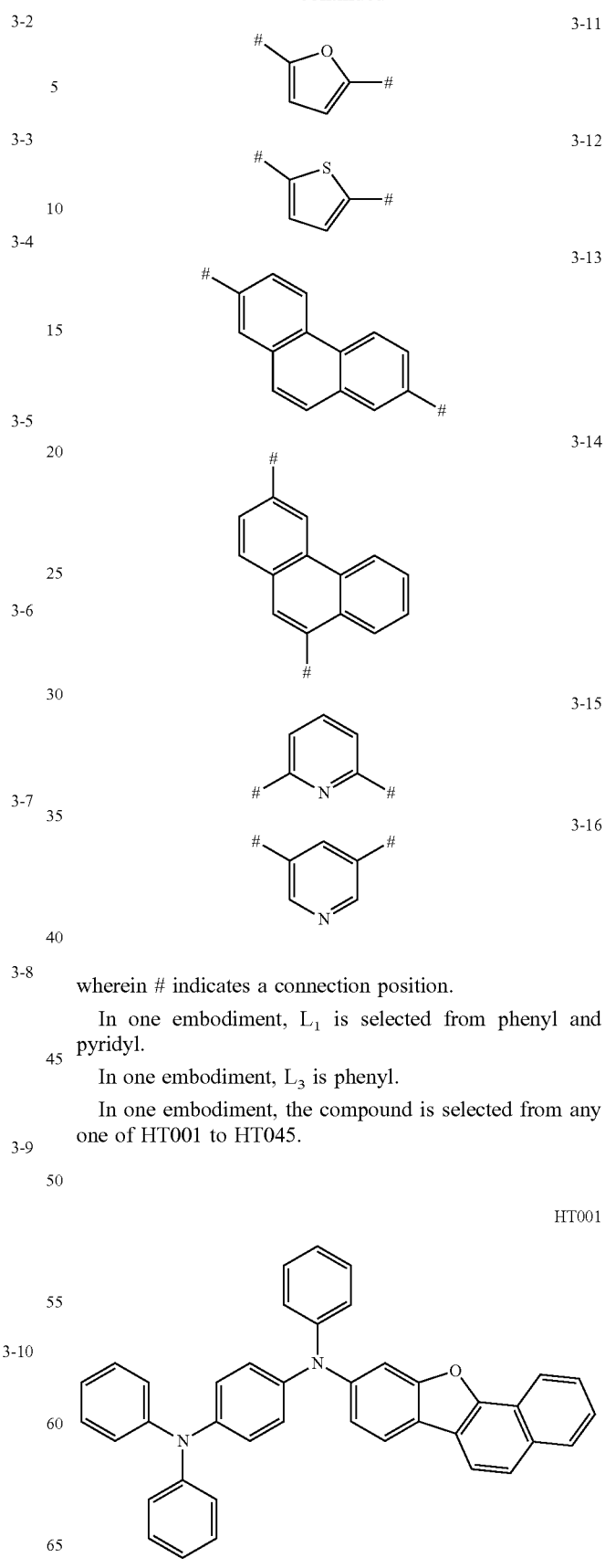
wherein # indicates a connection position.
In one embodiment, $L_1$ is selected from phenyl and pyridyl.
In one embodiment, $L_3$ is phenyl.
In one embodiment, the compound is selected from any one of HT001 to HT045.

HT002
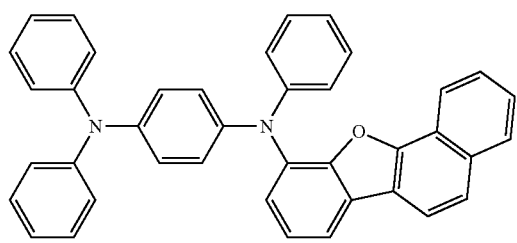
HT003
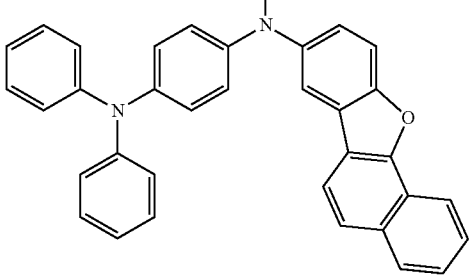
HT004
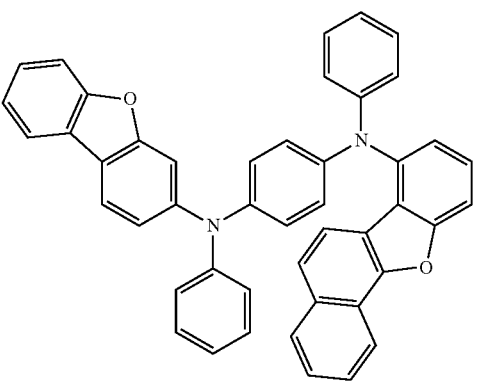
HT005
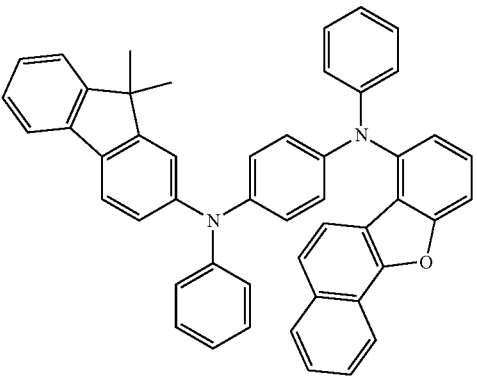
HT006
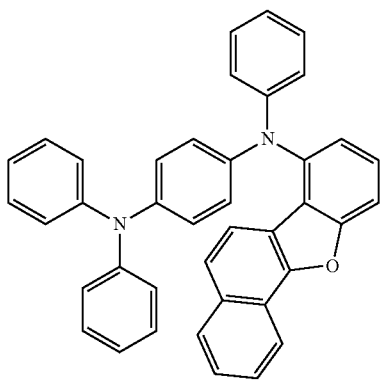
HT007
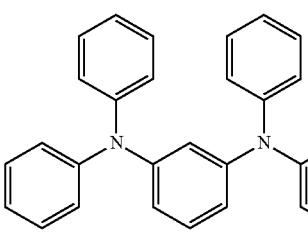
HT008
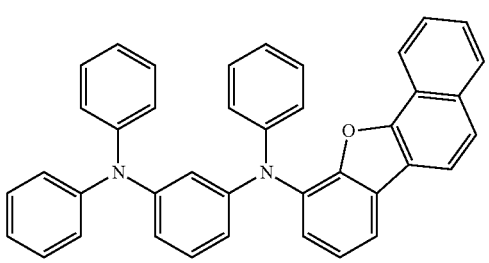
HT009
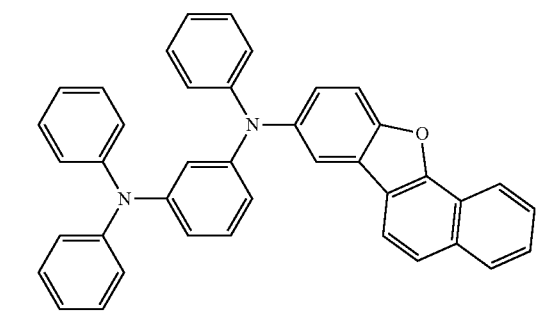
HT010
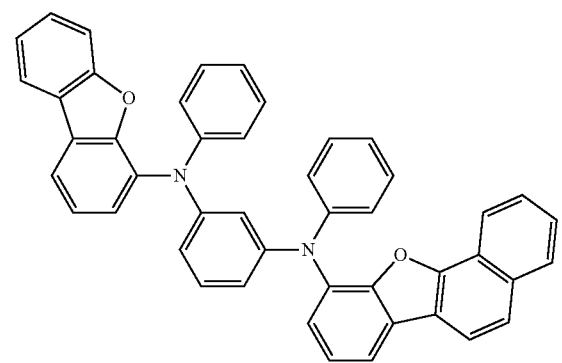

HT011
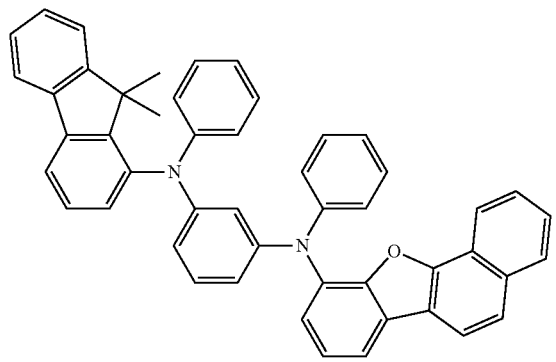
HT015
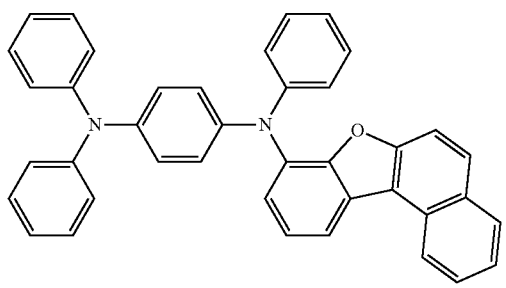
HT012
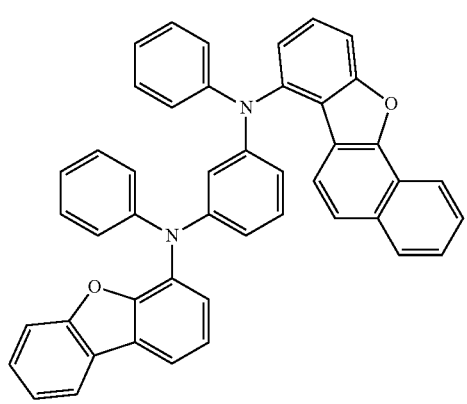
HT016
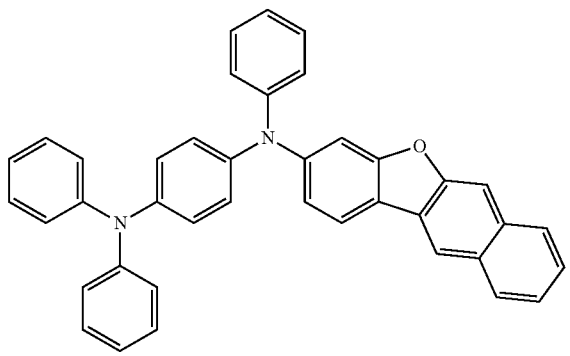
HT013
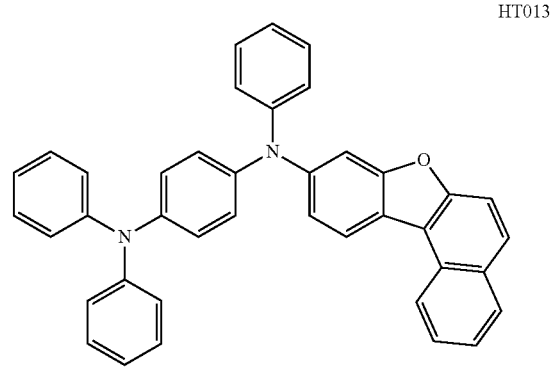
HT017
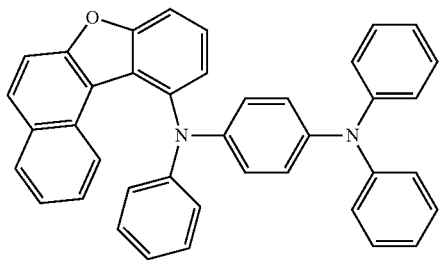
HT018
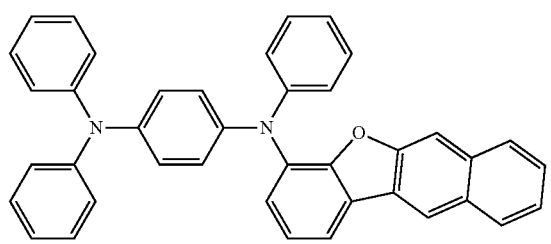
HT014
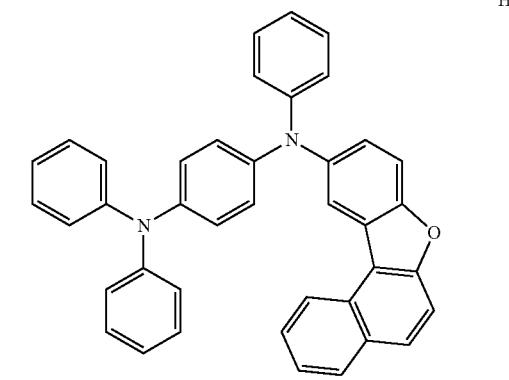
HT019
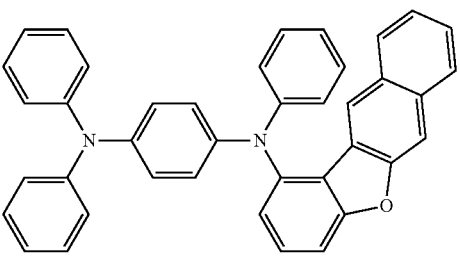

HT020
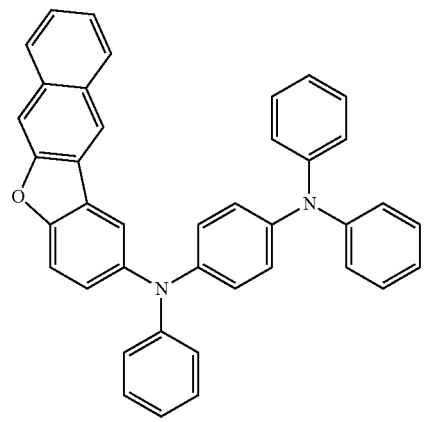
HT021
HT022
HT023
HT024
HT025
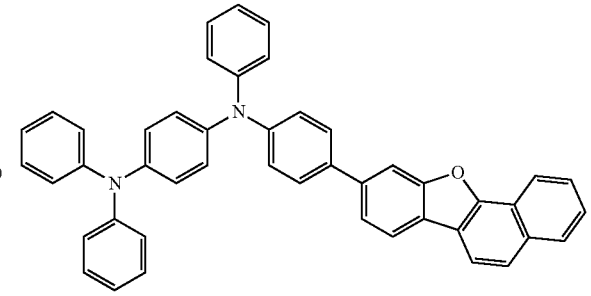
HT026
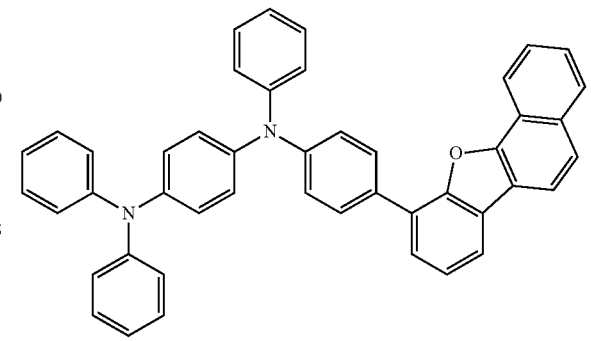
HT027
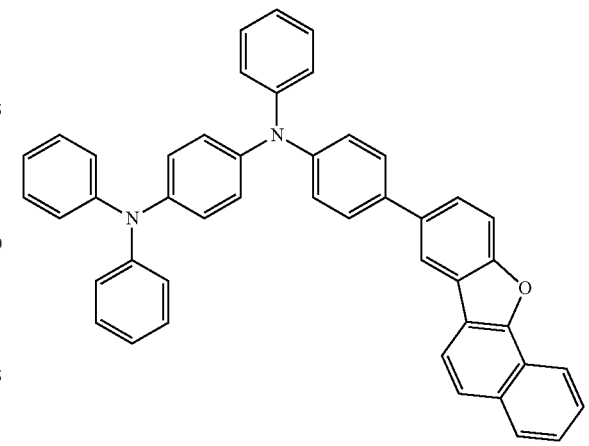
HT028
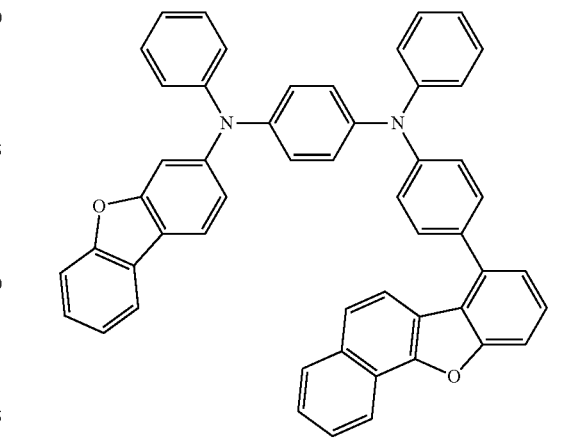

HT029
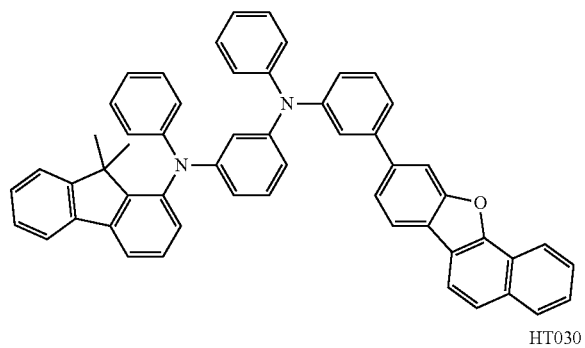
HT030
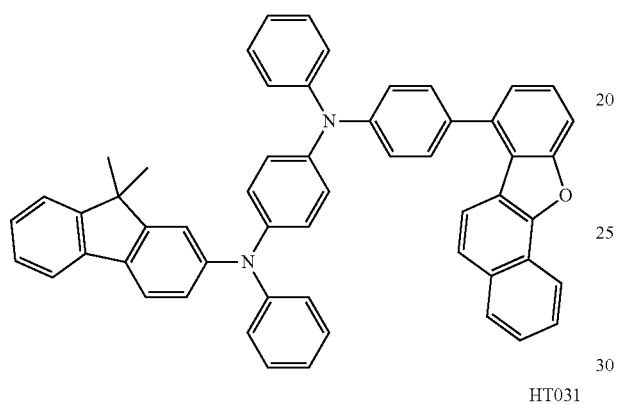
HT031
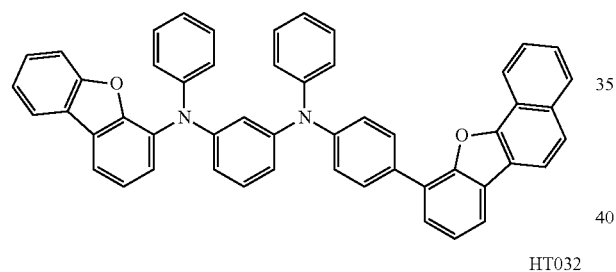
HT032
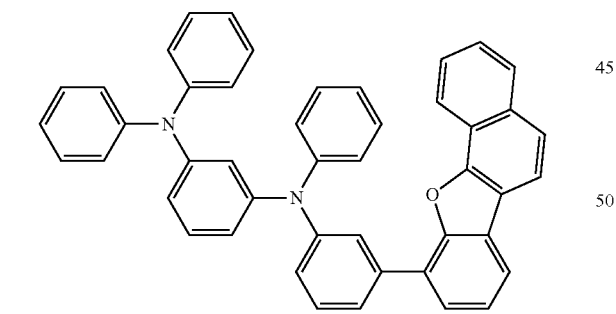
HT033
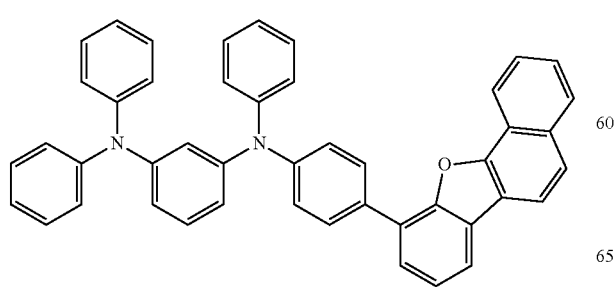
HT034
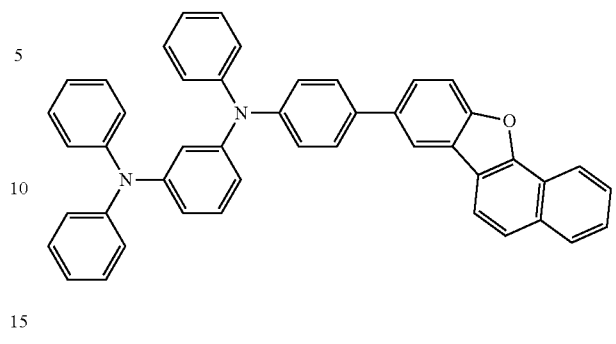
HT035
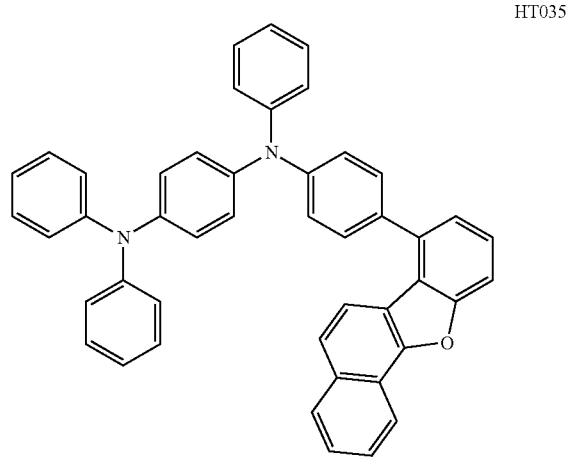
HT036
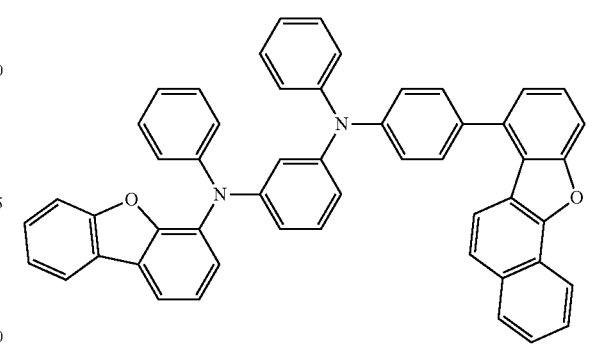
HT037
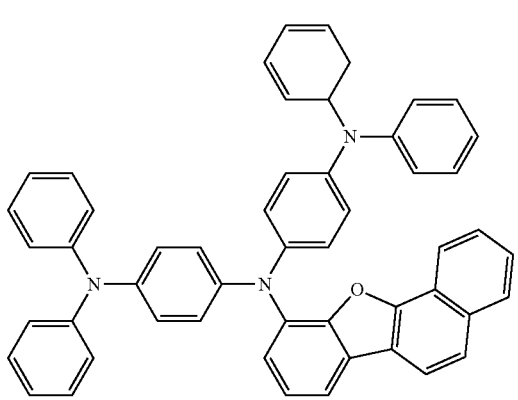

HT038
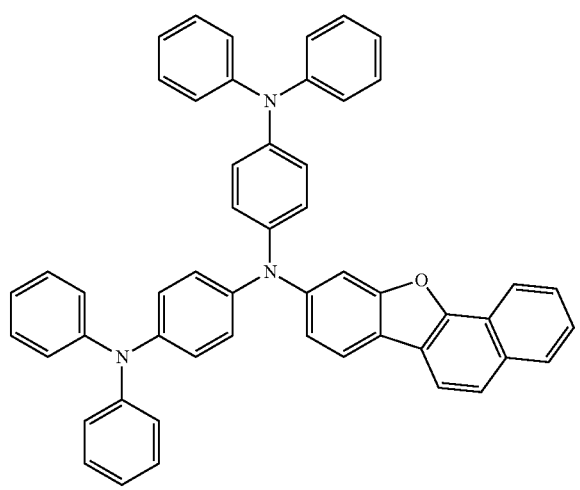
HT039
HT040
HT041
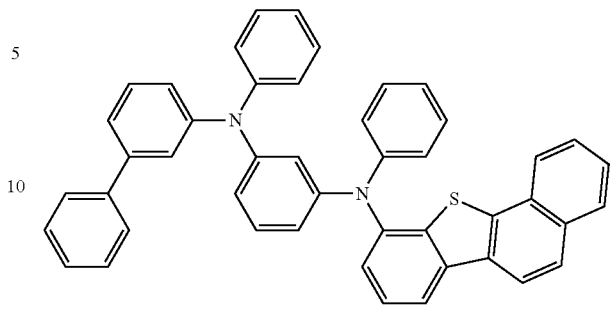
HT042
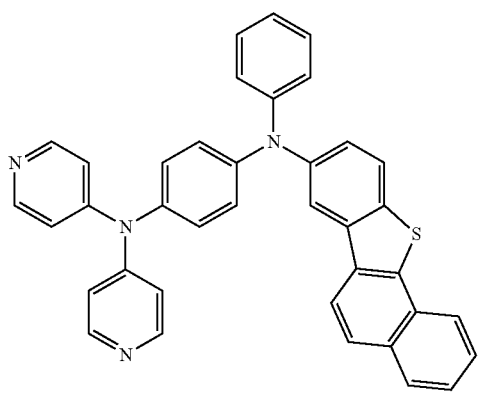
HT043
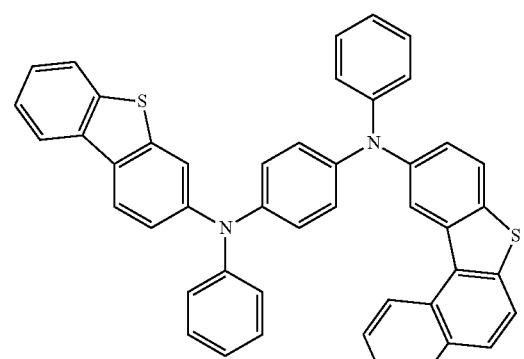
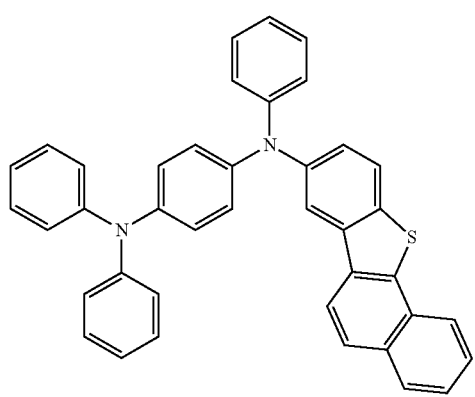
HT044
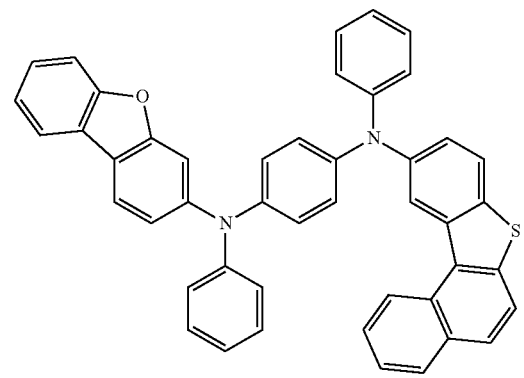

HT045

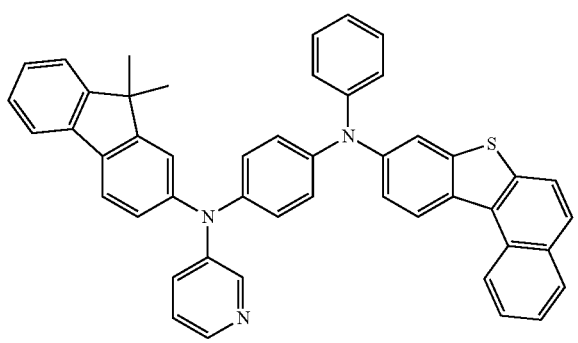

HT041

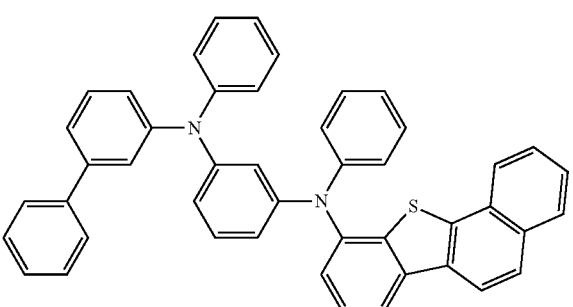

In one embodiment, the compound is selected from any one of HT002, HT012, HT030, HT041, and HT042.

HT002

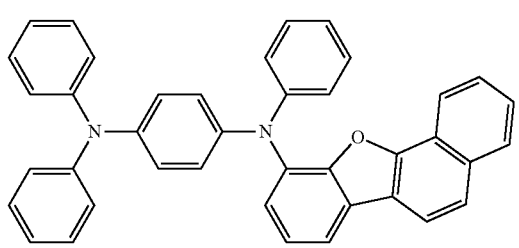

HT042

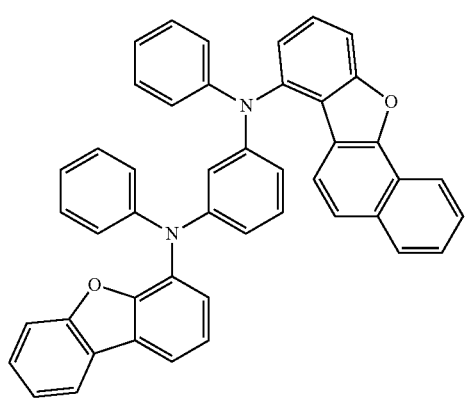

HT012

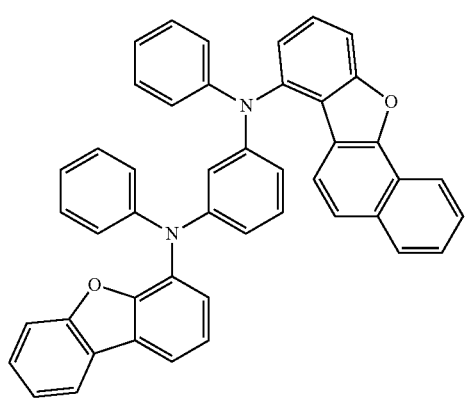

HT030

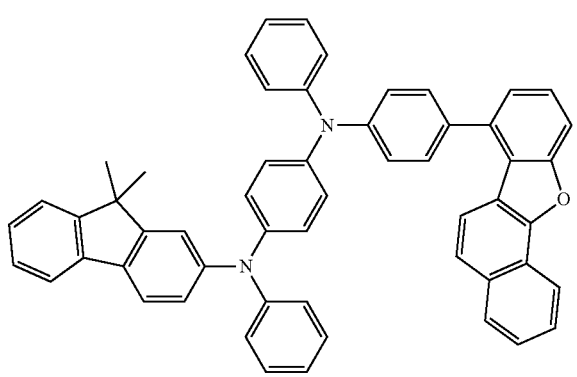

For compounds in the present disclosure, the presence of arylamine can ensure the matching of HOMO (Highest Occupied Molecular Orbital) energy levels. Compared with other electron donor groups of the same type, heteroaryl fluorenyl groups have a stronger electron-accepting ability, which ensures that heteroaryl-containing compounds have lower LUMO energy levels that can effectively block electrons from passing through a light-emitting layer, confine electrons in light-emitting regions, increase the recombination probability of electrons and holes, and thereby improve the efficiency and lifetime of a device. Also, the compounds disclosed herein have relatively distorted configuration, so that the materials have better solubility and film-forming properties.

In another embodiment, the present disclosure provides an organic electroluminescence device including a first electrode and a second electrode, and an organic functional layer between the first electrode and the second electrode. The organic functional layer includes a hole transport layer, wherein the hole transport layer is made of a material including the compound according to the present disclosure.

In one embodiment, the organic functional layer also includes a light-emitting compensation layer. The light-emitting compensation layer is made of a material including the compound according to the present disclosure.

In one embodiment, the organic electroluminescence device includes a substrate, an anode and a cathode opposite to each other, and an organic functional layer between the anode and the cathode. The organic functional layer includes an electron transport layer, a light-emitting compensation layer, a light-emitting layer, and a hole transport layer.

In one embodiment, the organic electroluminescence device is shown in FIG. 1, including a substrate 1, an ITO anode 2, a first hole transport layer 3, a second hole transport layer 4, a light-emitting compensation layer 5, a light-emitting layer 6, a first electron transport layer 7, a second electron transport layer 8, a cathode 9, and a capping layer 10.

The structure of the organic electroluminescent device may include a single light-emitting layer or multiple light-emitting layers.

The substrate may be a substrate in a conventional organic electroluminescent device, such as glass or plastic. The anode can be made of transparent and highly conductive materials, such as indium tin oxide (ITO), indium zinc oxide (IZO), tin dioxide (SnO2), and zinc oxide (ZnO).

The hole transport materials (HTM) of the hole transport layer are required to have high thermal stability (high Tg), high hole transport ability, and be capable of forming pinhole-free films by vacuum deposition. Commonly used HTMs are aromatic polyamine compounds, mainly tri-arylamine derivatives.

In a top-emitting device, the light-emitting compensation layer can effectively adjust the light color of a light-emitting target. Materials of the light-emitting compensation layer shall have a higher triplet energy level T1 which effectively blocks excitons generated in the light-emitting layer and reduces the generation of Joule heat, a higher HOMO energy level which effectively blocks electrons from passing through the light-emitting layer and improves device luminous efficiency, good thermal and electrochemical stabilities, and good film-forming properties.

The organic light-emitting layer includes host materials and guest materials. The guest materials are light-emitting materials, such as a dye. The host materials shall have the following characteristics: a reversible electrochemical redox potential, HOMO energy level and LUMO (Lowest Unoccupied Molecular Orbital) energy level matching adjacent hole transport layer and electron transport layer, good and matched hole and electron transport capabilities, good thermal stability, good film-forming capability, suitable singlet or triplet energy gaps for controlling excitons, and a good energy transferability with corresponding fluorescent dyes or phosphorescent dyes. The light-emitting materials of the organic light-emitting layer, taking a dye as an example, shall have the following characteristics: a high fluorescence or phosphorescent quantum efficiency, a good overlap between absorption spectrum of the dye and emission spectrum of the host (the host is compatible with the dye in terms of energy so that energy can be effectively transferred from the host to the dye), narrow emission peaks of red, green, and blue for achieving good color purity, good stability, and evaporation processable.

Electron transport materials (ETM) of the electron transport layer shall have reversible and sufficiently high electrochemical reduction potentials, suitable HOMO and LUMO energy levels so that electrons can be better injected, good hole-blocking abilities, high electron transport abilities, good film-forming properties, and good thermal stabilities. ETM generally include conjugated planar aromatic compounds with electron-deficient structures. The electron transport layer uses Alq3 (8-hydroxyquinoline aluminum) or TAZ (3-phenyl-4-(1'-naphthyl)-5-benzene-1,2,4-triazole) or TPBi (1,3,5-tris (N-phenyl-2-benzimidazole) benzene) or a combination of any two of these three materials.

There are two types of capping layer materials: electronic capping layer materials and hole capping layer materials. Compared with a hole-type capping layer, an electron-type capping layer has a relatively higher refractive index. This property can be used for designing capping layers. The main function of capping layers is to improve light extraction efficiency and adjust the efficiency of a top-emitting device (thicknesses of the capping layer have a great effect on efficiency). The capping layer shall have a high refractive index that is conducive to coupling with light and a small extinction coefficient in a region of 450 nm to visible light to prevent light from being absorbed by the capping layer itself.

In one embodiment, the organic electroluminescent device is manufactured by forming an anode (first electrode) on a transparent or opaque smooth substrate, forming an organic functional layer on the anode, and forming a cathode (second electrode) on the organic functional layer). The organic functional layer can be formed by a known film-forming method such as vapor deposition, sputtering, spin coating, dipping, and ion plating.

In another embodiment, the present disclosure provides a display device including the organic electroluminescent device according to the present disclosure.

Figure 2:
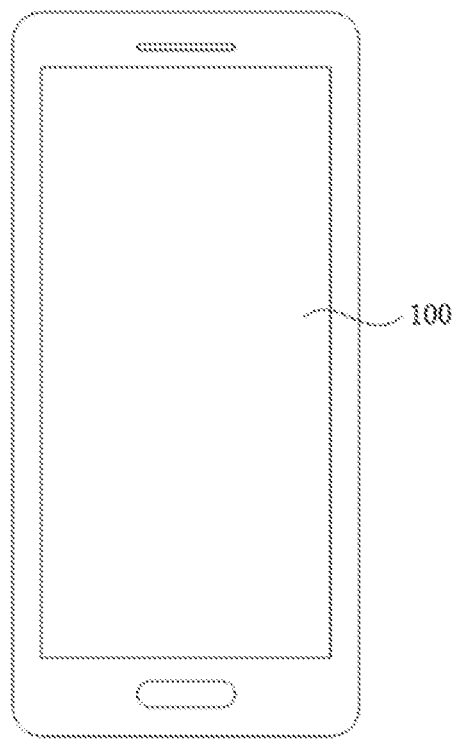
FIG. 2 illustrates an exemplary display screen of a mobile phone consistent with various disclosed embodiments of the present disclosure.

In one embodiment, the display device includes but not limited to a mobile phone, a computer, an LCD television, a smart watch, a smart car, a virtual reality (VR) or an augmented reality (AR) helmet. FIG. 2 illustrates a display screen of a mobile phone, wherein 100 represents a display screen.

The compound, the organic electroluminescent device, and the display device according to the present disclosure have many combinations. The embodiments of the present disclosure are only intended to describe the present disclosure in detail and are not intended to limit the present disclosure. The present disclosure will be described below in combination with an organic electroluminescent device containing the compound of the present disclosure as an example.

Exemplary Synthesis Embodiment 1: Synthesis of Compound HT002

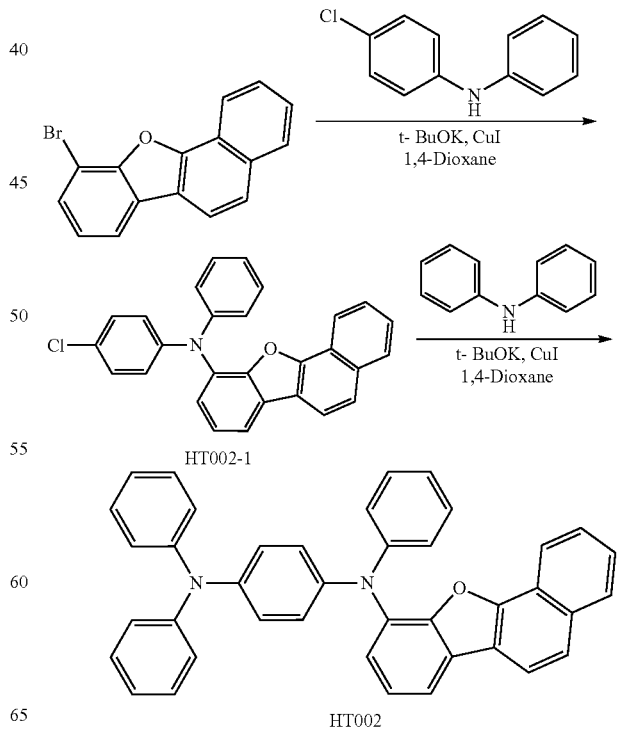

In a 250 mL round bottom flask, 12 mmol of 10-bromobenzo[b]naphtho[1,2-d]furan, 15 mmol of copper iodide, 65 mmol of potassium tert-butoxide, 12 mmol of 1,2-diaminocyclohexane, and 12 mmol of (4-chloro-phenyl)-phenylamine are added into 100 mL of dry 1,4-dioxane. The solution is refluxed for 48 hours under $N_2$ atmosphere to obtain an intermediate. The intermediate is cooled to room temperature, added into water, filtered through a pad of celite while being extracted with dichloromethane, washed with water, and dried using anhydrous magnesium sulfate. After filtration and evaporation, a crude product is purified by silica gel column chromatography to obtain intermediate product HT002-1.

In a 250 ml round bottom flask, 12 mmol of intermediate products HT002-1, 15 mmol of copper iodide, 65 mmol of potassium tert-butoxide, 12 mmol of 1,2-diaminocyclohexane, and 12 mmol of diarylamine are added into 100 mL of dry 1,4-dioxane. The solution is refluxed for 48 hours under $N_2$ atmosphere to obtain an intermediate. The intermediate is cooled to room temperature, added into water, filtered through a pad of celite while being extracted with dichloromethane, washed with water, and dried using anhydrous magnesium sulfate. After filtration and evaporation, a crude product is purified by silica gel column chromatography to obtain final product HT002.

Elemental analyses for the compound HT002 (molecular formula: $C_{40}H_{28}N_2O$) are as follows. Theoretical molecular weight of HT002 is 552.22, including 86.93% of C, 5.11% of H, 5.07% of N, and 2.89% of O. The tested molecular weight of HT002 by liquid chromatography-mass spectrometry analysis (ESI-MS (m/z) (M+) is 552.66, including 86.93% of C, 5.11% of H, 5.07% of N, and 2.89% of O.

Exemplary Synthesis Embodiment 2: Synthesis of Compound HT012

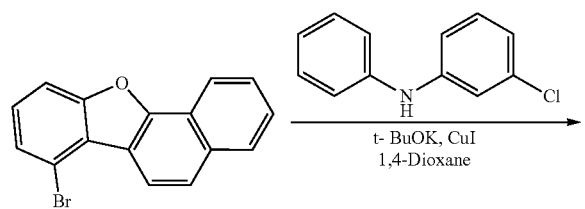

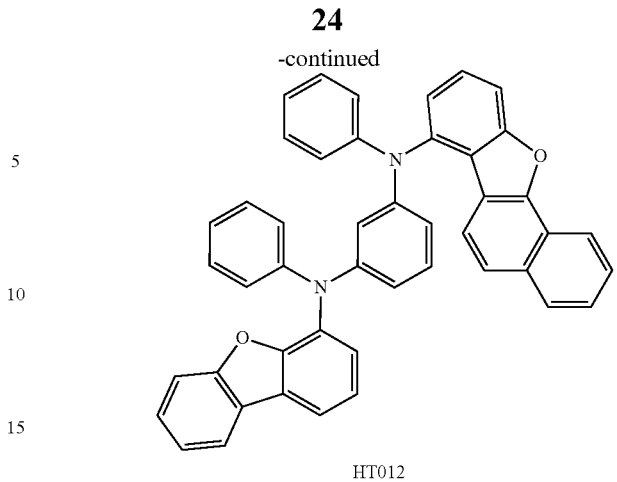

HT012

In a 250 mL round bottom flask, 12 mmol of 7-bromobenzo[b]naphtho[1,2-d]furan, 15 mmol of copper iodide, 65 mmol of potassium tert-butoxide, 12 mmol of 1,2-diaminocyclohexane, and 12 mmol of (4-chloro-phenyl)-phenylamine are added into 100 mL of dry 1,4-dioxane. The solution is refluxed for 48 hours under $N_2$ atmosphere to obtain an intermediate. The intermediate is cooled to room temperature, added into water, filtered through a pad of celite while being extracted with dichloromethane, washed with water, and dried using anhydrous magnesium sulfate. After filtration and evaporation, a crude product is purified by silica gel column chromatography to obtain intermediate product HT012-1.

In a 250 ml round bottom flask, 12 mmol of intermediate products HT012-1, 15 mmol of copper iodide, 65 mmol of potassium tert-butoxide, 12 mmol of 1,2-diaminocyclohexane, and 12 mmol of dibenzofuran-4-phenyl-amine are added into 100 mL of dry 1,4-dioxane. The solution is refluxed for 48 hours under $N_2$ atmosphere to obtain an intermediate. The intermediate is cooled to room temperature, added into water, filtered through a pad of celite while being extracted with dichloromethane, washed with water, and dried using anhydrous magnesium sulfate. After filtration and evaporation, a crude product is purified by silica gel column chromatography to obtain final product HT012.

Elemental analyses for the compound HT012 (molecular formula: $C_{46}H_{30}N_2O_2$) are as follows. Theoretical molecular weight of HT012 is 642.23, including 85.96% of C, 4.70% of H, 4.36% of N, and 4.98% of O. The tested molecular weight of HT012 by liquid chromatography-mass spectrometry analysis (ESI-MS (m/z) (M+) is 642.72, including 85.96% of C, 4.71% of H, 4.35% of N, and 4.98% of O.

Exemplary Synthesis Embodiment 3: Synthesis of Compound HT030

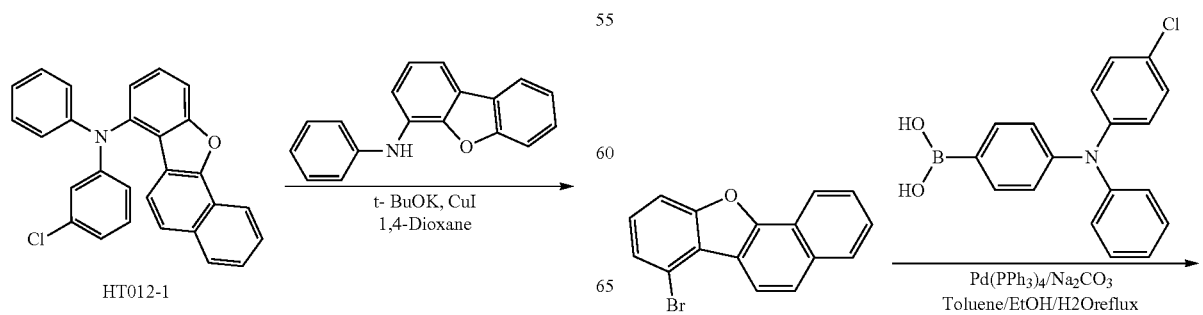

-continued

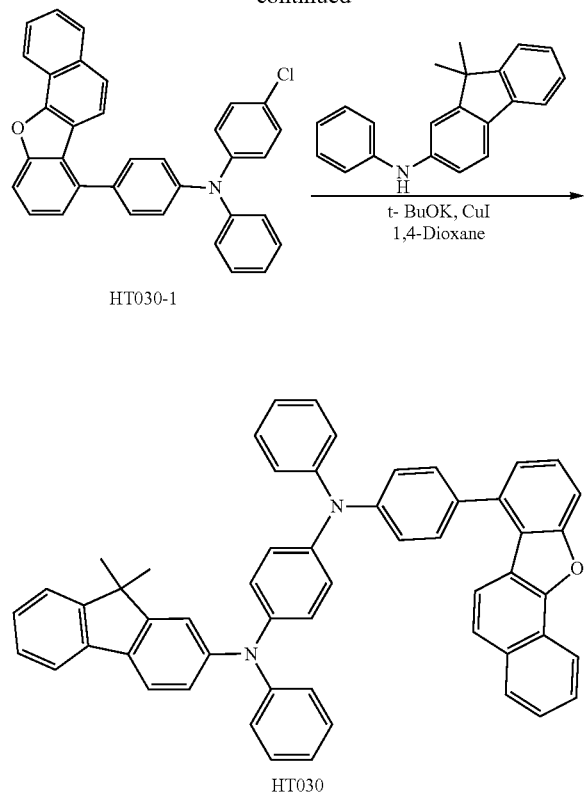

In a 250 mL round bottom flask, 12 mmol of 7-bromobenzo[b]naphtho[1,2-d]furan, 10 mmol of (4-Chlorophenyl)-(4-borate-phenyl)-phenylamine, and 80 mmol of $Na_2CO_3$ are separately added into 150 mL of toluene/EtOH (anhydrous ethanol)/$H_2O$ (volume ratio 75/25/50) to form a mixture. 0.48 mmol of $Pd(PPh_3)_4$ is added into the above mixture and refluxed for 20 hours under $N_2$ atmosphere to obtain an intermediate. The intermediate is cooled to room temperature, added into water, filtered through a pad of celite while being extracted with dichloromethane, washed with water, and dried using anhydrous magnesium sulfate. After filtration and evaporation, a crude product is purified by silica gel column chromatography to obtain intermediate product HT030-1.

In a 250 ml round bottom flask, 12 mmol of intermediate products HT030-1, 15 mmol of copper iodide, 65 mmol of potassium tert-butoxide, 12 mmol of 1,2-diaminocyclohexane, and 12 mmol of dimethylfluoren-2-phenyl-amine are added into 100 mL of dry 1,4-dioxane. The solution is refluxed for 48 hours under $N_2$ atmosphere to obtain an intermediate. The intermediate is cooled to room temperature, added into water, filtered through a pad of celite while being extracted with dichloromethane, washed with water, and dried using anhydrous magnesium sulfate. After filtration and evaporation, a crude product is purified by silica gel column chromatography to obtain final product HT030.

Elemental analyses for the compound HT030 (molecular formula: $C_{55}H_{40}N_2O$) are as follows. Theoretical molecular weight of HT030 is 744.31, including 88.68% of C, 5.41% of H, 3.76% of N, and 2.15% of O. The tested molecular weight of HT030 by liquid chromatography-mass spectrometry analysis (ESI-MS) (m/z) (M+) is 744.92, including 88.68% of C, 5.40% of H, 3.77% of N, and 2.15% of O.

Exemplary Synthesis Embodiment 4: Synthesis of Compound HT041

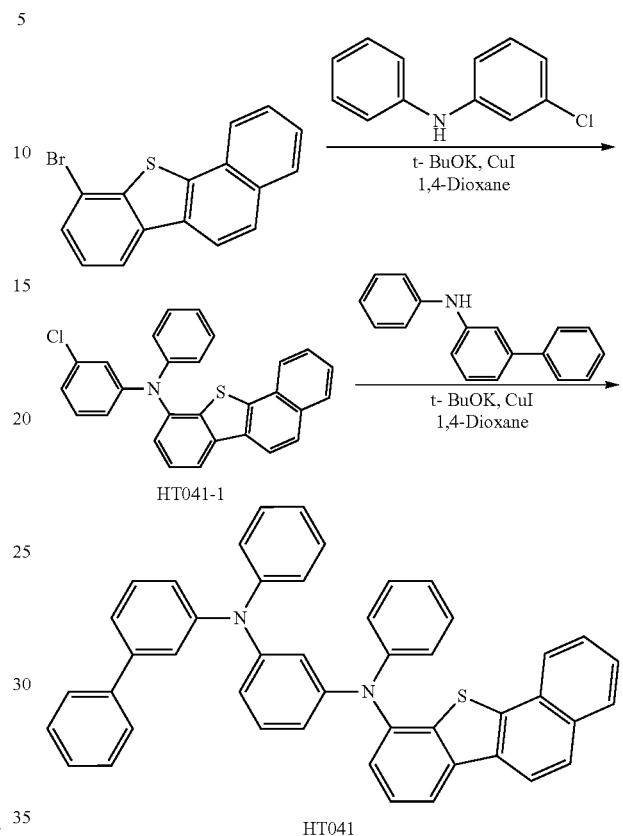

In a 250 mL round bottom flask, 12 mmol of 10-bromobenzo[b]naphtho[1,2-d]thiophene, 15 mmol of copper iodide, 65 mmol of potassium tert-butoxide, 12 mmol of 1,2-diaminocyclohexane, and 12 mmol of (3-chloro-phenyl)-phenylamine are added into 100 mL of dry 1,4-dioxane and refluxed for 48 hours under $N_2$ atmosphere to obtain an intermediate. The intermediate is cooled to room temperature, added into water, filtered through a pad of celite while being extracted with dichloromethane, washed with water, and dried using anhydrous magnesium sulfate. After filtration and evaporation, a crude product is purified by silica gel column chromatography to obtain intermediate product HT041-1.

In a 250 ml round bottom flask, 12 mmol of intermediate products HT041-1, 15 mmol of copper iodide, 65 mmol of potassium tert-butoxide, 12 mmol of 1,2-diaminocyclohexane, and 12 mmol of biphenyl-3-phenyl-amine are added into 100 mL of dry 1,4-dioxane. The solution is refluxed for 48 hours under $N_2$ atmosphere to obtain an intermediate. The intermediate is cooled to room temperature, added into water, filtered through a pad of celite while being extracted with dichloromethane, washed with water, and dried using anhydrous magnesium sulfate. After filtration and evaporation, a crude product is purified by silica gel column chromatography to obtain final product HT041.

Elemental analyses for the compound HT041 (molecular formula: $C_{46}H_{32}N_2S$) are as follows. Theoretical molecular weight of HT041 is 644.23, including 85.68% of C, 5.00% of H, 4.34% of N, and 4.97% of S. The tested molecular weight of HT041 by liquid chromatography-mass spectrometry analysis (ESI-MS (m/z) (M+) is 644.82, including 85.68% of C, 5.01% of H, 4.33% of N, and 4.97% of S.

Exemplary Synthesis Embodiment 5: Synthesis of Compound HT042

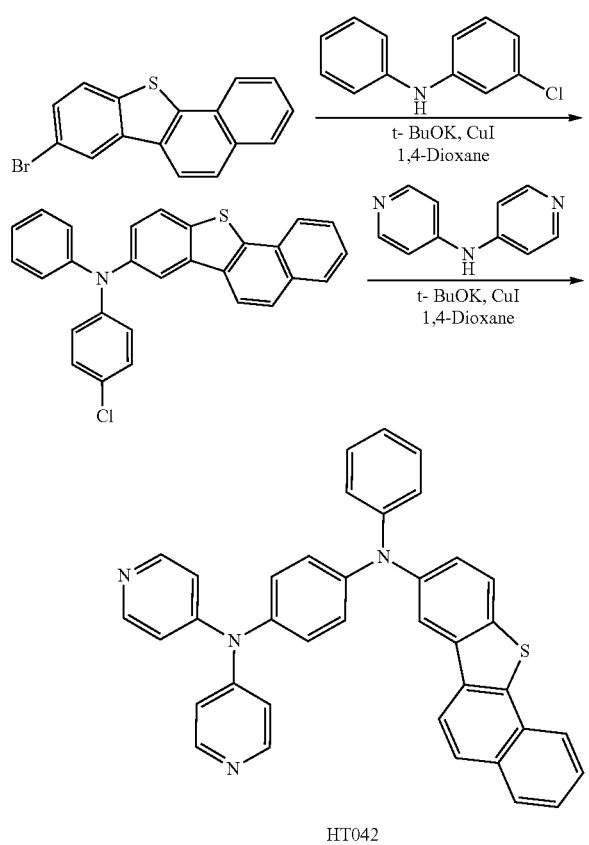

HT042

In a 250 mL round bottom flask, 12 mmol of 8-bromobenzo[b]naphtho[1,2-d]thiophene, 15 mmol of copper iodide, 65 mmol of potassium tert-butoxide, 12 mmol of 1,2-diaminocyclohexane, and 12 mmol of (3-chloro-phenyl)-phenylamine are added into 100 mL of dry 1,4-dioxane and refluxed for 48 hours under $N_2$ atmosphere to obtain an intermediate. The intermediate is cooled to room temperature, added into water, filtered through a pad of celite while being extracted with dichloromethane, washed with water, and dried using anhydrous magnesium sulfate. After filtration and evaporation, a crude product is purified by silica gel column chromatography to obtain intermediate product HT042-1.

In a 250 ml round bottom flask, 12 mmol of intermediate products HT042-1, 15 mmol of copper iodide, 65 mmol of potassium tert-butoxide, 12 mmol of 1,2-diaminocyclohexane, and 12 mmol of dipyridyl-amine are added into 100 mL of dry 1,4-dioxane. The solution is refluxed for 48 hours under $N_2$ atmosphere to obtain an intermediate. The intermediate is cooled to room temperature, added into water, filtered through a pad of celite while being extracted with dichloromethane, washed with water, and dried using anhydrous magnesium sulfate. After filtration and evaporation, a crude product is purified by silica gel column chromatography to obtain final product HT042.

Elemental analyses for the compound HT042 (molecular formula: $C_{38}H_{26}N_4S$) are as follows. Theoretical molecular weight of HT042 is 570.19, including 79.97% of C, 4.59% of H, 9.82% of N, and 5.62% of S. The tested molecular weight of HT041 by liquid chromatography-mass spectrometry analysis (ESI-MS (m/z) (M+) is 570.70, including 79.97% of C, 4.59% of H, 9.82% of N, and 5.62% of S.

Compound Simulations

Energy level differences between singlet stage and triplet stage of an organic material can be simulated by Gaussian 09 software (Gaussian Inc.). A detailed simulation method of energy level differences $\Delta E_{st}$ may refer to J. Chem. Theory Comput., 2013, DOI: 10.1021/ct400415r. An optimized molecular structure and activation can be obtained by using TD-DFT method "B3LYP" and base group "6-31g(d)". Glass transition temperatures ($T_g$) of the compounds are measured by differential scanning calorimetry. In this disclosure, the compounds obtained from synthesis embodiments 1-5 are simulated and calculated. In comparison, a chemical NPB (molecular structure is shown below) is simulated and calculated in a comparative embodiment. The simulation results are shown in Table 1.

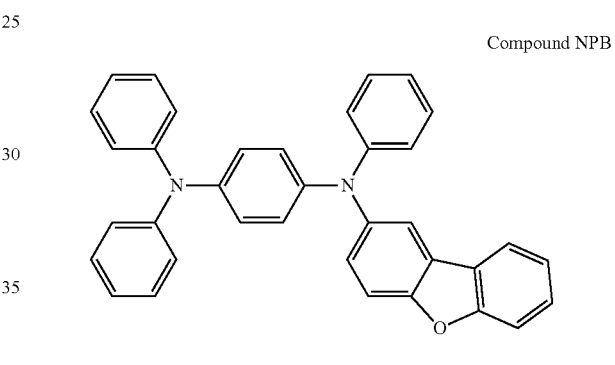

Compound NPB

TABLE 1

| Number | Compound number | HOMO (eV) | LUMO (eV) | Eg (eV) | $E_T$ (eV) | Tg (° C.) |
|---|---|---|---|---|---|---|
| Embodiment 1 | HT002 | −5.01 | −2.23 | 3.78 | 2.69 | 127 |
| Embodiment 2 | HT012 | −5.03 | −2.25 | 3.78 | 2.68 | 124 |
| Embodiment 3 | HT030 | −5.04 | −2.21 | 3.83 | 2.70 | 120 |
| Embodiment 4 | HT041 | −508 | −2.26 | 3.82 | 2.66 | 123 |
| Embodiment 5 | HT042 | −5.07 | −2.29 | 3.78 | 2.68 | 126 |
| Comparative embodiment 1 | NPB | −5.52 | −2.42 | 3.10 | 2.58 | 98 |

It can be seen from Table 1 that the triplet energy levels of all the compounds from synthesis embodiments are greater than 2.65 eV, which is higher than the triplet state of the comparative embodiment 1. $T_g$ values of all the compounds from synthesis embodiments are greater than 120° C., which is a significant improvement compared to that of comparative embodiment 1. HOMO energy levels and LUMO energy levels of all the compounds from synthesis embodiments match well with energy levels of adjacent layer materials used in mass production.

Exemplary Device Embodiment 1: Blue Organic Electroluminescence Device (Hole Transport Layer)

One embodiment provides an organic electroluminescence device. The organic electroluminescence device includes a substrate 1, an ITO anode 2, a first hole transport layer 3, a second hole transport layer 4, a light-emitting compensation layer 5, a light-emitting layer 6, a first electron transport layer 7, a second electron transport layer 8, a cathode 9 (magnesium-silver electrode with a Mg—Ag mass ratio of 9:1), and a capping layer (CPL) 10, where a thickness of the ITO anode 2 is 15 nm, a thickness of the first hole transport layer 3 is 10 nm, a thickness of the second hole transport layer 4 is 95 nm, a thickness of the light-emitting compensation layer 5 is 90 nm, a thickness of the light-emitting layer 6 is 30 nm, a thickness of the first electron transport layer 7 is 30 nm, a thickness of the second electron transport layer 8 is 5 nm, a thickness of the magnesium-silver electrode 9 is 15 nm, and a thickness of the CPL 10 is 100 nm.

In one embodiment, forming the organic electroluminescence device includes:

1) cutting a substrate 1 having an ITO anode 2 into a size of 50 mm×50 mm×0.7 mm; ultrasonically treating the substrate in isopropyl alcohol and deionized water, respectively, for 30 minutes; exposing the substrate to ozone for approximately 10 minutes to clean the substrate; and mounting the substrate having the ITO anode 2 on a vacuum deposition equipment;

2) on the ITO anode 2, depositing the HT002 obtained in the exemplary synthesis embodiment 1 and HAT-CN (molecular structure is shown below) by a vacuum evaporation method to form a hole buffer layer with a thickness of 10 nm, and this layer is used as the first hole transport layer 3;

3) on the first hole transport layer 3, depositing the HT002 obtained in the exemplary synthesis embodiment 1 by vacuum evaporation to form a layer with a thickness of 95 nm, and this layer is used as the second hole transport layer 4;

4) on the second hole transport layer 4, depositing the material NPB by vacuum evaporation to form a layer with a thickness of 90 nm, and this layer is used as the light-emitting compensation layer 5;

5) on the light-emitting compensation layer 5, depositing the light-emitting layer 6 having CBP (molecular structure is shown below) as a host material and FIrpic (molecular structure is shown below) as a doping material, the mass ratio of CBP and FIrpic is 97:3, and the thickness of the light-emitting layer 6 is 30 nm;

6) on the light-emitting layer 6, depositing Alq3 (molecular structure is shown below) by vacuum evaporation to form the first electron transport layer 7 with a thickness of 30 nm.

7) on the first electron transport layer 7, depositing LiF by vacuum evaporation to form the second electron transport layer 8 with a thickness of 5 nm;

8) on the second electron transport layer 8, depositing magnesium and silver by vacuum evaporation to form the cathode 9 with a thickness of 15 nm, wherein the mass ratio of Mg—Ag is 9:1; and 9) on the cathode 9, depositing high-refractive hole-type material CBP by vacuum evaporation to form the capping layer with a thickness of 100 nm.

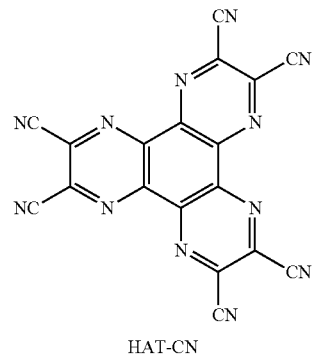

HAT-CN

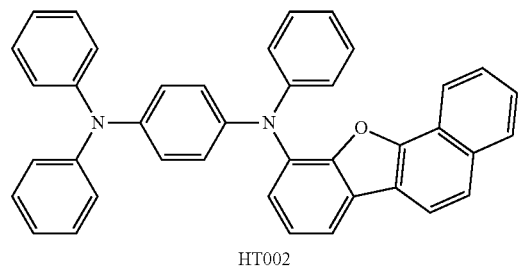

HT002

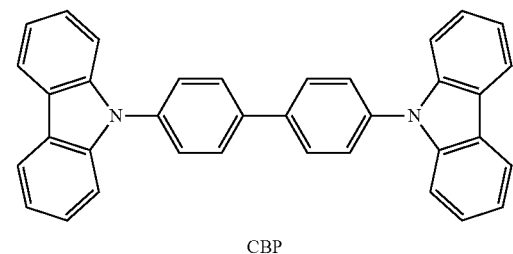

CBP

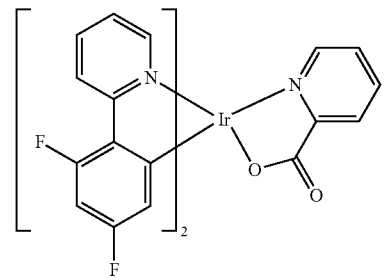

FIrpic

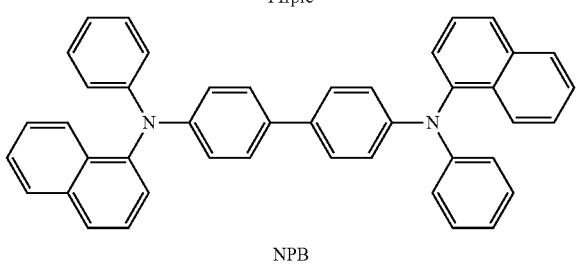

NPB

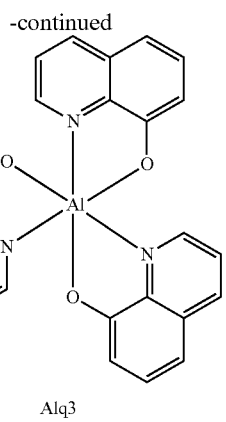

Alq3

Exemplary Device Embodiment 2

Compared with device embodiment 1, forming a device in exemplary device embodiment 2 is the same except that HT002 is replaced with HT012 in the first hole transport layer 3 and the second hole transport layer 4.

Exemplary Device Embodiment 3

Compared with device embodiment 1, forming a device in exemplary device embodiment 3 is the same except that HT002 is replaced with HT030 in the first hole transport layer 3 and the second hole transport layer 4.

Exemplary Device Embodiment 4

Compared with device embodiment 1, forming a device in exemplary device embodiment 4 is the same except that HT002 is replaced with HT041 in the first hole transport layer 3 and the second hole transport layer 4.

Exemplary Device Embodiment 5

Compared with device embodiment 1, forming a device in exemplary device embodiment 5 is the same except that HT002 is replaced with HT042 in the first hole transport layer 3 and the second hole transport layer 4.

Device Comparative Embodiment 1

Compared with device embodiment 1, forming a device in device comparative embodiment 1 is the same except that HT002 is replaced with NPB in the first hole transport layer 3 and the second hole transport layer 4.

Driving voltages, light-emitting efficiencies, and lifetimes of devices obtained from different embodiments are tested and summarized in Table 2. Compared with device comparative embodiment 1, OLED display devices provided by the present disclosure have lower driving voltages, higher light-emitting efficiencies, and longer lifetimes, wherein the driving voltages are less than 3.80 V, the light-emitting efficiencies are greater than 69 (current efficiency, Cd/A), and the lifetimes are greater than 60 h. Compared with device comparative embodiment 1, the voltages are increased by about 5%, the efficiencies are increased by 7.5%, and the lifetimes are increased by more than 6%. These notable performance improvements are mainly due to materials of the present disclosure having higher triplet energy levels (>2.65 eV) and suitable HOMO values that match well with adjacent layers, which can effectively transport holes to the light-emitting layer to effectively combine with electrons to emit light.

TABLE 2

Testing results of devices obtained from different embodiments

| Number | HT material | Driving voltage (V) | E/CIEy | Lifetime LT95 (hrs) (@50 mA/cm$^2$) |
|---|---|---|---|---|
| Device embodiment 1 | HT002 | 3.78 | 69.4 | 66 |
| Device embodiment 2 | HT012 | 3.79 | 69.6 | 64 |
| Device embodiment 3 | HT030 | 3.77 | 69.1 | 64 |
| Device embodiment 4 | HT041 | 3.80 | 69.9 | 65 |
| Device embodiment 5 | HT042 | 3.78 | 70.5 | 65 |
| Device comparative embodiment 1 | NPB | 4.05 | 63.8 | 60 |

Exemplary Device Embodiment 6, Blue Organic Electroluminescence Device (Light-Emitting Compensation Layer)

One embodiment provides an organic electroluminescence device. The organic electroluminescence device includes a substrate 1, an ITO anode 2, a first hole transport layer 3, a second hole transport layer 4, a light-emitting compensation layer 5, a light-emitting layer 6, a first electron transport layer 7, a second electron transport layer 8, a cathode 9 (magnesium-silver electrode with a Mg—Ag mass ratio of 9:1), and a capping layer (CPL) 10, where a thickness of the ITO anode 2 is 15 nm, a thickness of the first hole transport layer 3 is 10 nm, a thickness of the second hole transport layer 4 is 95 nm, a thickness of the light-emitting compensation layer 5 is 90 nm, a thickness of the light-emitting layer 6 is 30 nm, a thickness of the first electron transport layer 7 is 30 nm, a thickness of the second electron transport layer 8 is 5 nm, a thickness of the magnesium-silver electrode 9 is 15 nm, and a thickness of the CPL 10 is 100 nm.

In one embodiment, forming the organic electroluminescence device includes:
1) cutting a substrate 1 having an ITO anode 2 into a size of 50 mm×50 mm×0.7 mm; ultrasonically treating the substrate in isopropyl alcohol and deionized water, respectively, for 30 minutes; exposing the substrate to ozone for approximately 10 minutes to clean the substrate; and mounting the substrate having the ITO anode 2 on a vacuum deposition equipment;
2) on the ITO anode 2, depositing HAT-CT (molecular structure is shown below) and TAPC (molecular structure is shown below) by a vacuum evaporation method to form a layer with a thickness of 10 nm, and this layer is used as the first hole transport layer 3;
3) on the first hole transport layer 3, depositing TAPC (molecular structure is shown below) by vacuum evaporation to form a layer with a thickness of 95 nm, and this layer is used as the second hole transport layer 4;
4) on the second hole transport layer 4, depositing the material HT002 obtained from the synthesis embodiment 1 by vacuum evaporation to form a layer with a thickness of 90 nm, and this layer is used as the light-emitting compensation layer 5;
5) on the light-emitting compensation layer 5, depositing the light-emitting layer 6 having CBP (molecular structure is shown below) as a host material and FIrpic (molecular structure is shown below) as a doping material, the mass ratio of CBP and FIrpic is 97:3, and the thickness of the light-emitting layer 6 is 30 nm;

6) on the light-emitting layer 6, depositing Alq3 (molecular structure is shown below) by vacuum evaporation to form the first electron transport layer 7 with a thickness of 30 nm;

7) on the first electron transport layer 7, depositing LiF by vacuum evaporation to form the second electron transport layer 8 with a thickness of 5 nm;

8) on the second electron transport layer 8, depositing magnesium and silver by vacuum evaporation to form the cathode 9 with a thickness of 15 nm, wherein the mass ratio of Mg—Ag is 9:1; and 9) on the cathode 9, depositing high-refractive hole-type material CBP by vacuum evaporation to form the capping layer with a thickness of 100 nm.

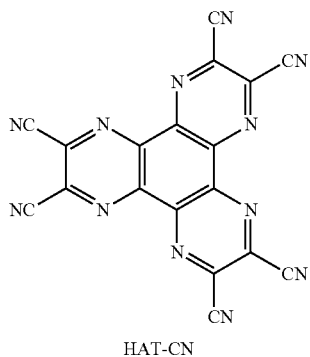

HAT-CN

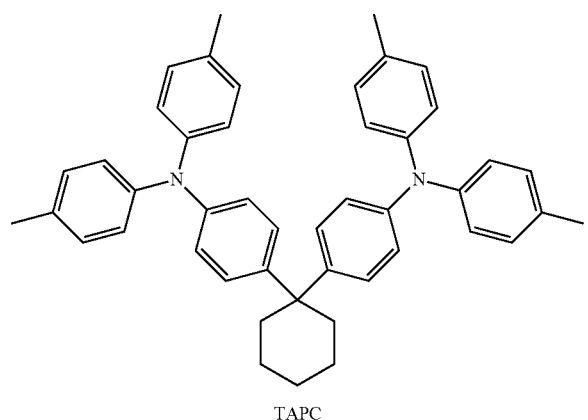

TAPC

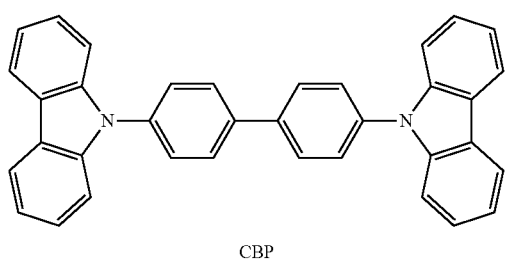

CBP

-continued

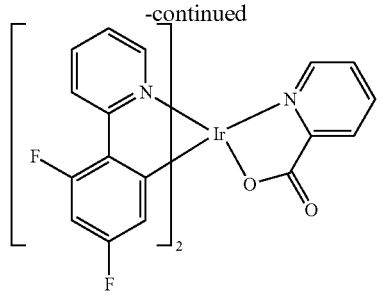

FIrpic

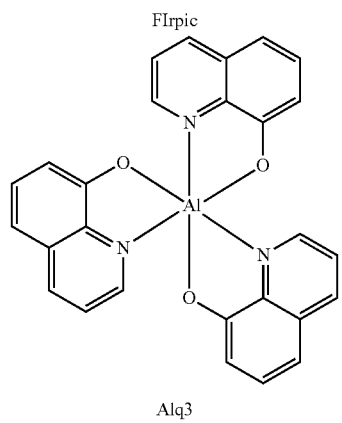

Alq3

Exemplary Device Embodiment 7

Compared with device embodiment 6, forming a device in device embodiment 7 is the same except that HT002 is replaced with HT012 in the light-emitting compensation layer 5.

Exemplary Device Embodiment 8

Compared with device embodiment 6, forming a device in device embodiment 8 is the same except that HT002 is replaced with HT030 in the light-emitting compensation layer 5.

Exemplary Device Embodiment 9

Compared with device embodiment 6, forming a device in device embodiment 9 is the same except that HT002 is replaced with HT041 in in the light-emitting compensation layer 5.

Exemplary Device Embodiment 10

Compared with device embodiment 6, forming a device in device embodiment 10 is the same except that HT002 is replaced with HT042 in the light-emitting compensation layer 5.

Device Comparative Embodiment 2

Compared with exemplary device embodiment 6, forming a device in device comparative embodiment 2 is the same except that HT002 is replaced with NPB in the light-emitting compensation layer 5.

Driving voltages, light-emitting efficiencies, and lifetimes of devices obtained from different embodiments are tested and summarized in Table 3. Compared with device comparative embodiment 2, OLED display devices provided by the present disclosure have lower driving voltages, higher light-emitting efficiencies, and longer lifetimes, wherein the driving voltages are approximately 3.80 V, the light-emitting efficiencies are approximately 69 Cd/A (current efficiency), and the lifetimes are greater than 67 h. Compared with device comparative embodiment 2, the voltages are increased by about 5%, the efficiencies are increased by 7.5%, and the lifetimes are increased by more than 8%. These notable performance improvements are mainly due to materials of the present disclosure having lower LUMO values and suitable HOMO values that match well with adjacent layers, which can effectively block electrons from passing through the light-emitting layer and confine the electrons inside the light-emitting layer to effectively recombine with holes. The improvements are also due to materials' high triplet energy levels (>2.65 eV), which can effectively block the backflow of excitons, improve the utilization of excitons, and effectively reduce the generation of non-radiative energy.

TABLE 3

Test results of devices obtained from different device embodiments

| Number | Light-emitting compensation layer | Driving voltage (V) | E/CIEy | Lifetime LT95 (hrs) (@50 mA/cm$^2$) |
|---|---|---|---|---|
| Device embodiment 6 | HT002 | 3.81 | 68.9 | 67 |
| Device embodiment 7 | HT012 | 3.82 | 69.1 | 68 |
| Device embodiment 8 | HT030 | 3.80 | 68.8 | 67 |
| Device embodiment 9 | HT041 | 3.84 | 69.2 | 69 |
| Device embodiment 10 | HT042 | 3.86 | 69.0 | 68 |
| Device comparative embodiment 2 | NPB | 3.98 | 65.1 | 62 |

As disclosed, the technical solutions of the present disclosure have the following advantages. The compounds according to the present disclosure have higher glass transition temperatures Tg and better thermal stabilities and electrochemical stabilities, which ensure the devices with good stability, and improve the lifetime of devices. These compounds have high triplet energy levels, matching well with energy levels of adjacent layer materials used in mass production to achieve effective energy transfer and limit excitons to light-emitting regions. These compounds have low LUMO values, which can restrict electrons to light-emitting regions, prevent electrons from crossing the light-emitting layer, reduce the generation of Joule heat, and improve the light-emitting efficiencies and lifetimes of devices.

The embodiments disclosed herein are exemplary only. Other applications, advantages, alternations, modifications, or equivalents to the disclosed embodiments are obvious to those skilled in the art and are intended to be encompassed within the scope of the present disclosure.

What is claimed is:

1. A compound having a formula (01):

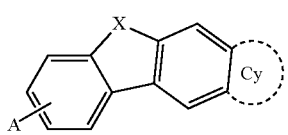

formula (01)

wherein:

X represents oxygen atom or sulfur atom;

$C_y$ represents substituted or unsubstituted C5-C40 aryl and is bound to 2- and 3-positions of a dibenzofuran or dibenzothiophene group; and A includes a structure represented by formula (II):

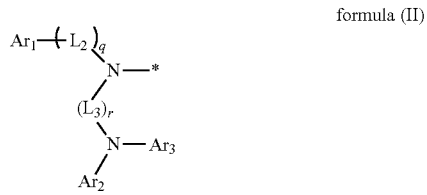

formula (II)

wherein each of $L_2$ and $L_3$ is independently selected from substituted or unsubstituted C5-C40 aryl, or substituted or unsubstituted C3-C40 heteroaryl; each of $Ar_1$, $Ar_2$, and $Ar_3$ is independently selected from substituted or unsubstituted C5-C40 aryl, substituted or unsubstituted C3-C40 heteroaryl, or substituted or unsubstituted arylamine containing one or two nitrogen atoms, and at least one of Ar1, Ar2, and Ar3 is independently selected from substituted or unsubstituted arylamine containing one or two nitrogen atoms;

at most one of Ar1, Ar2, and Ar3 includes a fluorene-containing group;

q is selected from 0 or 1, and r is 1; and

\* indicates a connection position.

2. The compound according to claim 1, wherein the substituted or unsubstituted C3-C40 heteroaryl for each of Ar1, Ar2, and Ar3 contains a heteroatom, the heteroatom including one or more selected from P, S, N, O, B, and Si.

3. The compound according to claim 1, wherein Cy is phenyl.

4. The compound according to claim 1, wherein one of $Ar_1$ and $L_3$ or both $Ar_1$ and $L_3$ are phenyl.

5. The compound according to claim 1, wherein each of $Ar_2$ and $Ar_3$ is independently selected from any one of phenyl, biphenyl, dibenzofuranyl, fluorenyl, and pyridyl.

6. The compound according to claim 1, wherein each of $L_2$ and $L_3$ is independently selected from one of the following:

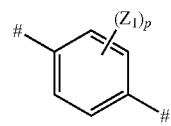

2-1

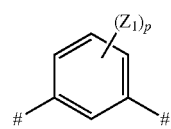

2-2

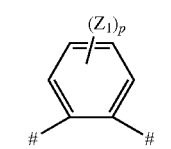

2-3

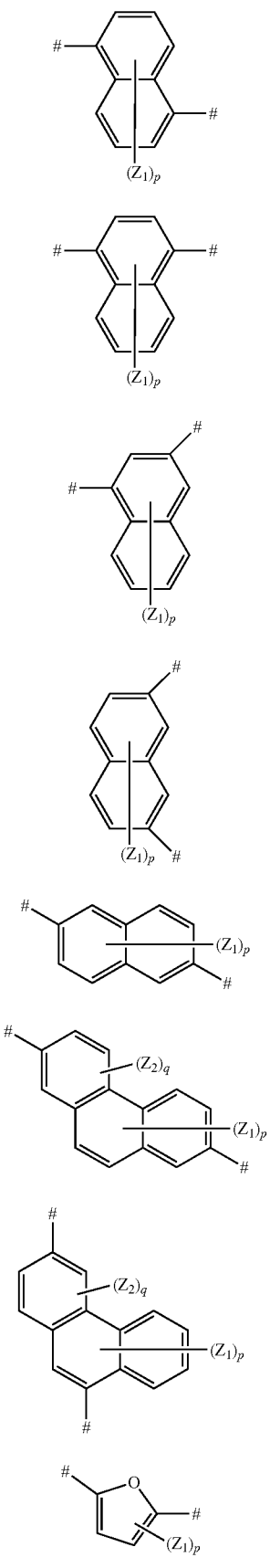
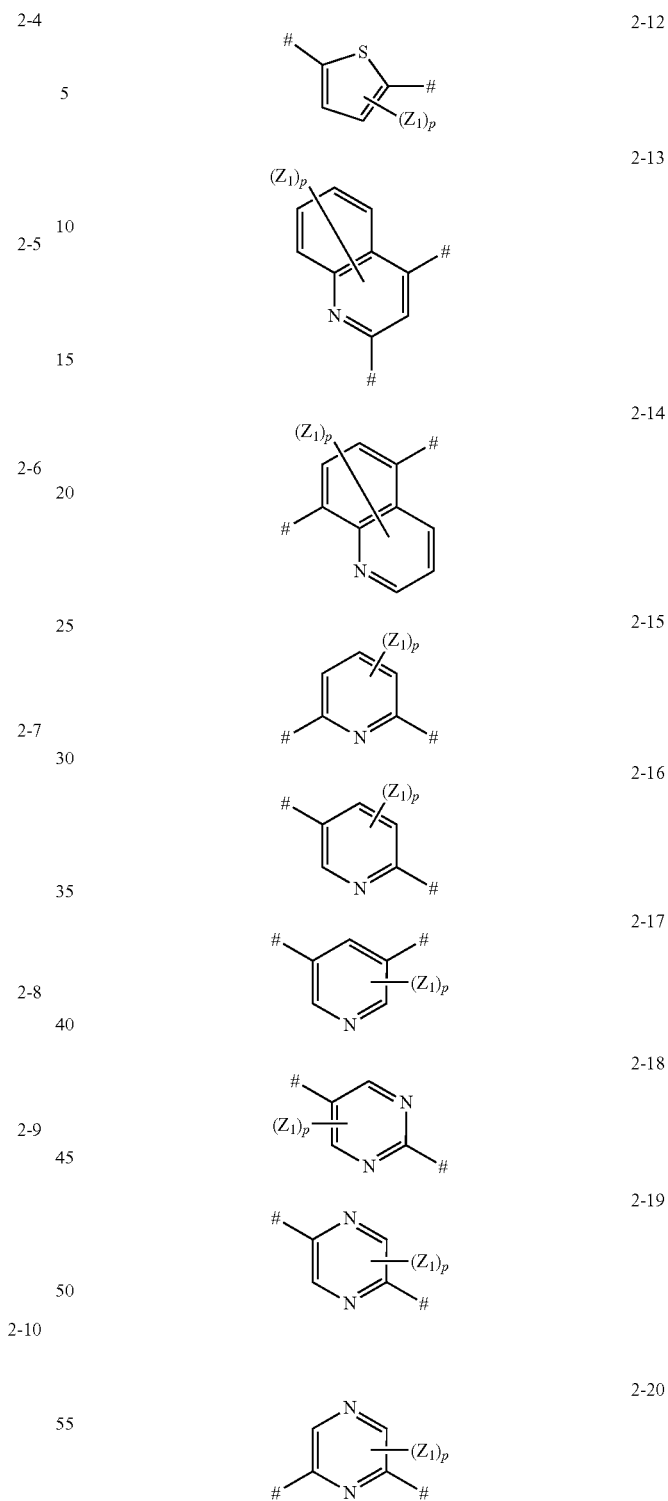
wherein $Z_1$ is selected from substituted or unsubstituted C5-C40 aryl, or substituted or unsubstituted C3-C40 heteroaryl, p is selected from 0, 1 or 2, and # indicates a connection position.
7. The compound according to claim 1, wherein each of $L_2$ and $L_3$ is independently selected from one of the following:

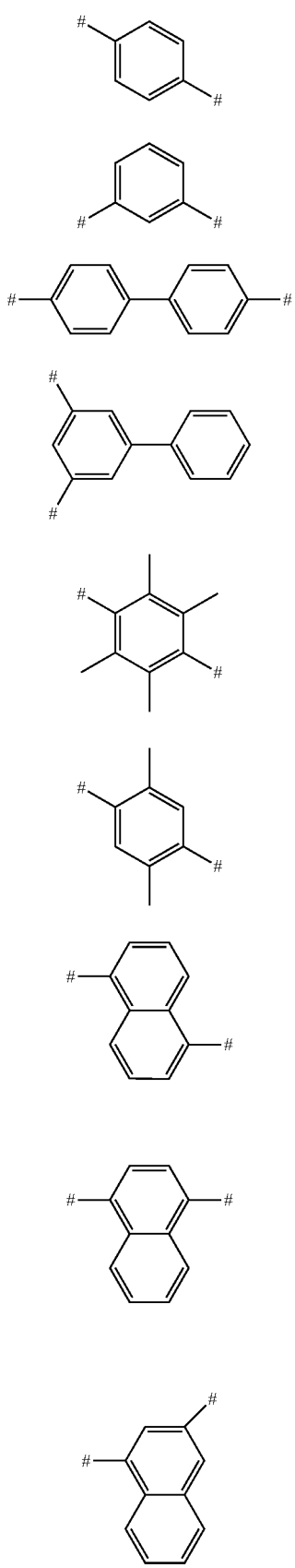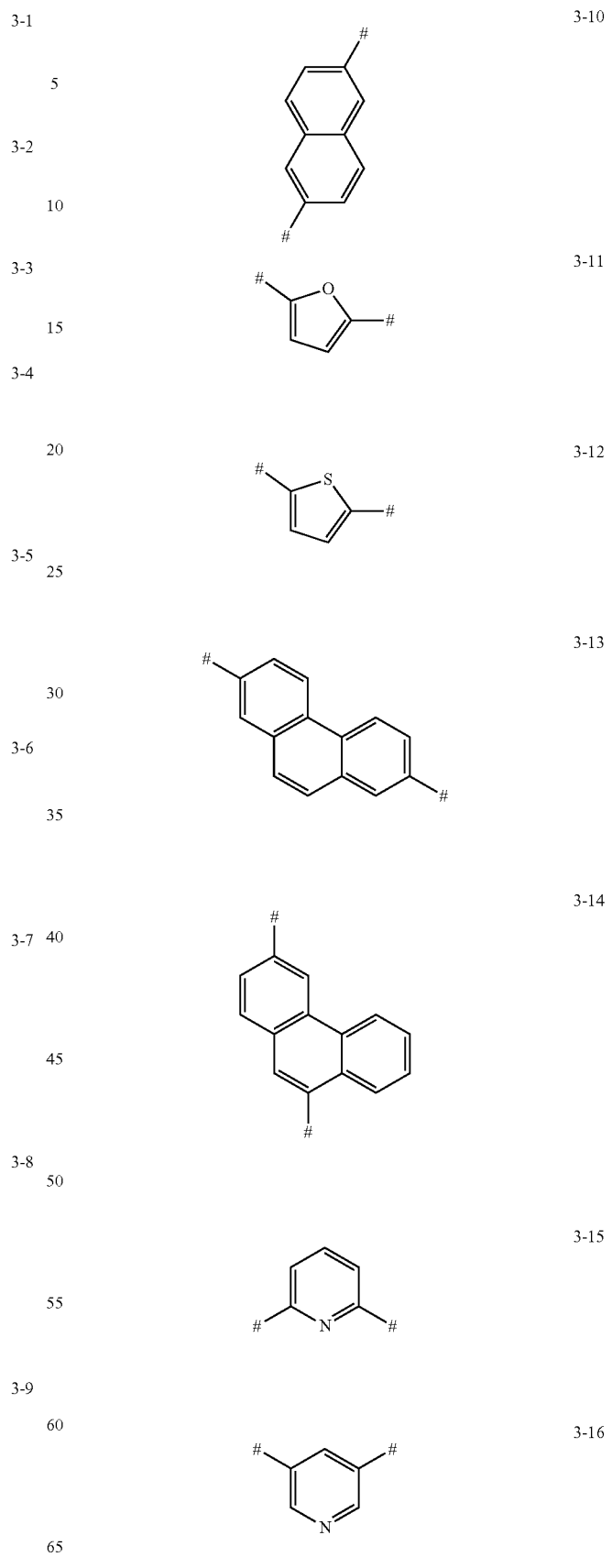
wherein # indicates a connection position.

8. A compound, wherein the compound is selected from:

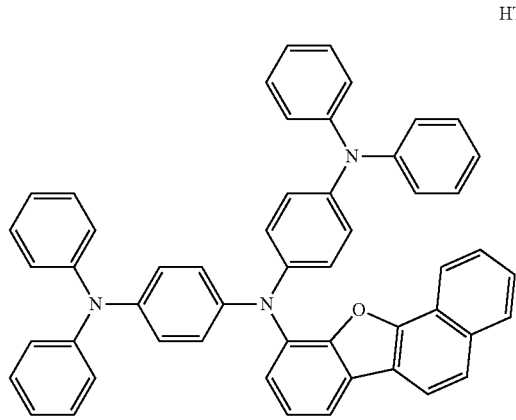
HT037

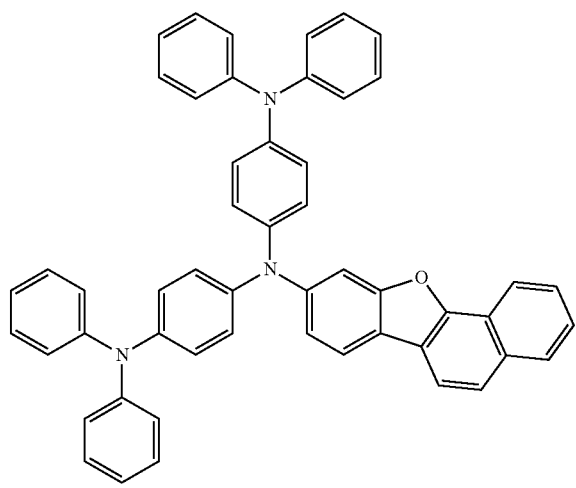
HT038

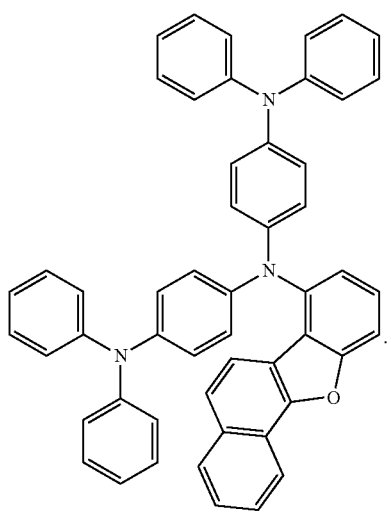
HT039

9. An organic electroluminescence device, comprising:
a first electrode and a second electrode, and an organic functional layer between the first electrode and the second electrode,
wherein the organic functional layer comprises a hole transport layer, wherein the hole transport layer is made of a material including a compound comprising the compound according to claim 1.

10. The organic electroluminescence device according to claim 9, wherein the organic functional layer further includes a light-emitting compensation layer, and the light-emitting compensation layer is made of a material including the compound having the formula (O1).

11. A display device comprising the organic electroluminescent device according to claim 9.

12. An organic electroluminescence device, comprising:
a first electrode and a second electrode, and an organic functional layer between the first electrode and the second electrode,
wherein the organic functional layer comprises a hole transport layer, wherein the hole transport layer is made of a material including a compound comprising the compound according to claim 8.

13. The organic electroluminescence device according to claim 12, wherein the organic functional layer further includes a light-emitting compensation layer, and the light-emitting compensation layer is made of a material including the compound according to claim 8.

14. A display device comprising the organic electroluminescent device according to claim 12.

* * * * *